United States Patent
Fik et al.

(10) Patent No.: US 11,433,004 B2
(45) Date of Patent: Sep. 6, 2022

(54) DENTAL COMPOSITION

(71) Applicant: DENTSPLY SIRONA Inc., York, PA (US)

(72) Inventors: Christoph Fik, Schonenberg a.d.Thur (CH); Sven Pohle, Constance (DE); Joachim E. Klee, Radolfzell (DE); Marina Barudzija, Stockach (DE); Magnus Schmidt, Donaueschingen (DE); Markus Ringwald, Constance (DE)

(73) Assignee: DENTSPLY SIRONA INC., York, PA (US)

( * ) Notice: Subject to any disclaimer, the term of this patent is extended or adjusted under 35 U.S.C. 154(b) by 880 days.

(21) Appl. No.: 16/303,176

(22) PCT Filed: May 19, 2017

(86) PCT No.: PCT/EP2017/062158
§ 371 (c)(1),
(2) Date: Nov. 20, 2018

(87) PCT Pub. No.: WO2017/198843
PCT Pub. Date: Nov. 23, 2017

(65) Prior Publication Data
US 2020/0323743 A1    Oct. 15, 2020

(30) Foreign Application Priority Data
May 20, 2016   (EP) .................................. 16170584

(51) Int. Cl.
*A61K 6/887* (2020.01)
*A61K 6/898* (2020.01)
*C08L 33/26* (2006.01)

(52) U.S. Cl.
CPC .............. *A61K 6/887* (2020.01); *A61K 6/898* (2020.01); *C08L 33/26* (2013.01)

(58) Field of Classification Search
CPC combination set(s) only.
See application file for complete search history.

(56) References Cited

U.S. PATENT DOCUMENTS

| | | | | |
|---|---|---|---|---|
| 5,480,790 A | * | 1/1996 | Tischer | A61K 47/61 530/410 |
| 5,891,862 A | * | 4/1999 | Mandeville, III | C07H 13/04 536/123 |
| 6,187,762 B1 | * | 2/2001 | Mandeville, III | C07H 15/04 514/23 |
| 2009/0022862 A1 | * | 1/2009 | Fluckiger | A23L 19/18 426/310 |
| 2009/0318622 A1 | * | 12/2009 | Migonney | C08L 51/10 525/50 |
| 2013/0164709 A1 | * | 6/2013 | Yang | A61K 6/30 554/59 |
| 2016/0038382 A1 | * | 2/2016 | Kawashima | A61K 6/884 523/115 |
| 2020/0323743 A1 | * | 10/2020 | Fik | A61K 6/813 |

* cited by examiner

*Primary Examiner* — Peter A Salamon
(74) *Attorney, Agent, or Firm* — Dentsply Sirona Inc.

(57) ABSTRACT

The present invention relates to a dental composition comprising
(i) an acidic polymerizable compound of the following formula (Ia), (Ib) or (Ic):

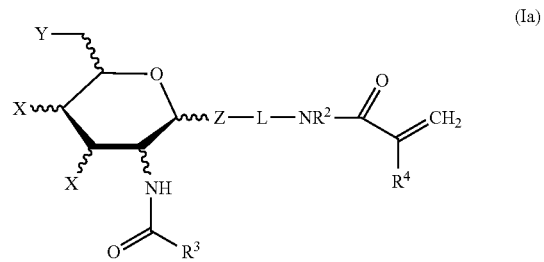
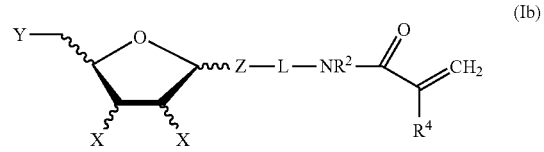
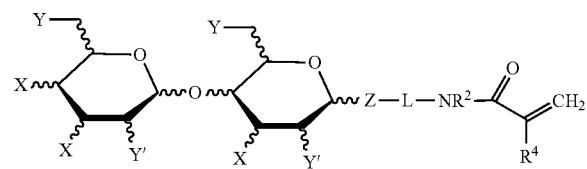

wherein X, Y, Y', Z, L, $R^2$, $R^3$ and $R^4$ are as defined in claim 1; and
(ii) an initiator system. Furthermore, the present invention relates to the use of the polymerizable compound of formula (I) for the preparation of a dental composition.

11 Claims, No Drawings

DENTAL COMPOSITION

FIELD OF THE INVENTION

The present invention relates to a dental composition comprising a specific acidic polymerizable compound and a process for preparing the compound. Furthermore, the present invention relates to the use of the specific acidic polymerizable compound for the preparation of a dental composition. The specific acidic polymerizable compound of the present invention has a 5- or 6-membered cyclic group containing an oxygen atom in the ring, such as a mono- or di-saccharide group.

BACKGROUND OF THE INVENTION

Polymerizable dental compositions containing polymerizable compounds are known. Conventionally, polymerizable dental compositions are provided for a broad range of applications and must, therefore, meet diverse requirements. For example, a polymerizable dental composition may be a dental adhesive composition, a bonding agent, a pit and fissure sealant, a dental desensitizing composition, a pulp capping composition, a dental composite, dental glass ionomer cement, a dental cement, a dental root canal sealer composition or a dental infiltrant.

Typically, (meth)acrylates, (meth)acrylamides and allylic ethers are used as polymerizable components in polymerizable dental compositions. (Meth)acrylates are particularly preferred due to their excellent reactivity in radical polymerizations which may be demonstrated based on the polymerization enthalpy in the range of from $\Delta_R H = -80$ to $-120$ kJ/mol. In order to provide crosslinking capability, polyfunctional (meth)acrylates such as bis-GMA, were used for dental applications as early as 1962.

In the field of dental compositions, components derived from saccharides are also known.

JP 2000-044421 A discloses a dental adhesive composition for preventing infection with bacteria, and JP 2000-178111 A discloses a kit of adhesive for dentistry. The dental adhesive composition and the kit may contain a non-ionic surfactant represented by lauryl alcohol typified by polyethylene sorbitan monolaurate fatty acids or higher fatty amines or polyethylene glycol type or polypropylene glycol type nonionic surfactants obtained by adding ethylene oxide or propylene oxide to aliphatic amides such as oleic acid amide, glycerol, pentaerythritol.

JP H05-07859 B2 and JP 2009-040772 A disclose a polymerizable composition for dental use comprising a polymerizable monomer in the form of a polyhydric alcohol in which one or more (meth)acrylate groups are bonded to secondary hydroxyl group(s) of the polyhydric alcohol.

JP H05-260093 B2 and JP 2009-215217 A disclose a hydrophilic polymerizable monomer for dental use, which monomer has a tetrahydrofuran ring or a furanose ring. In JP 2009-215217 A, as a specific example of the hydrophilic polymerizable monomer, a mixture of α-and β-anomer of 3,5,6-tri-O-methacryloyloxy-D-glucofuranose is disclosed.

WO 2008/114621 A1 discloses a polymerizable compound for dental use having polymerizable group(s) and hydroxyl groups. The polymerizable compound has a sugar alcohol skeleton containing polymerizable group(s) including (meth)acrylate groups as well as hydroxyl groups in a high density. The polymerizable compound may be prepared from a sugar alcohol.

WO 2012/036838 A2 discloses a saccharide amide compound and a dental composition comprising the saccharide amide compound. The saccharide amide compound comprises a hydrophobic group and at least one free-radically polymerizable group with the proviso that the hydrophobic group is not bonded to an ethylenically unsaturated carbon atom of the free-radically polymerizable group.

EP 2 979 679 A1 discloses a dental curable composition including a sugar compound having having an -XM group, where -X is an acid anion group and M is a metal cation.

SUMMARY OF THE INVENTION

It is the problem of the present invention to provide a dental composition comprising an acidic polymerizable compound copolymerizable with conventional polymerizable compounds such as (meth)acrylates, (meth)acrylamides and allylic ethers, and which compound provides an excellent adhesion to hard dental tissue including dentine and enamel, and very good biocompatibility.

The present invention provides a dental composition comprising
(i) an acidic polymerizable compound of the following formula (Ia), (Ib) or (Ic):

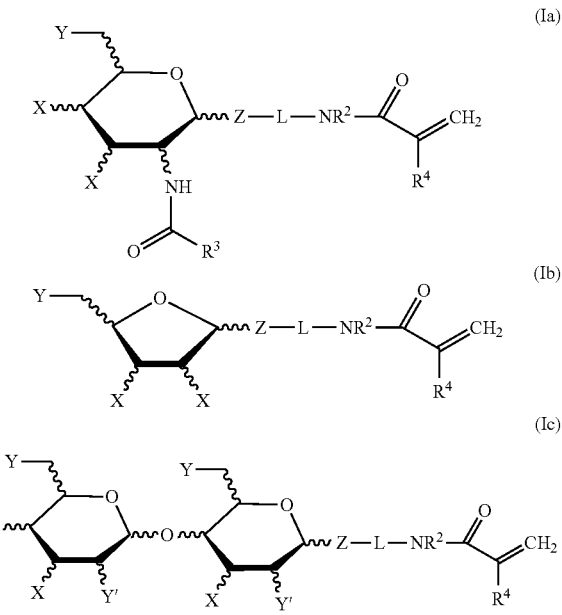

wherein
X which may be the same or different, are bonded directly or through a methylene group to the cyclic moiety, independently represent an acidic group selected from a sulfate group, a phosphate group, a sulfonate group, a phosphonate group and a carboxylic acid group;
Y represents, if present, a hydrogen atom, a methyl group, a hydroxyl group, an amino group, a polymerizable group, a thiol group or an amide group, each group Y is bonded directly or through a methylene group to the cyclic moiety;
Y' represents an OH or amide group —NH—(C=O)—R³, and
Z represents a single bond, a carbamate group, a thiocarbamate group, a dithiocarbamate group, a urea group, a thiourea group, an amide group, an oxygen atom, a sulfur atom, or a group NR', wherein R¹ represents a hydrogen atom, a straight-chain $C_{1-6}$ alkyl group, or a branched or cyclic $C_{3-6}$ alkyl group which may be substituted with a phosphonate group, wherein group Z is bonded directly or through a methylene group to the cyclic moiety, L represents a divalent linker group;

R² represents a hydrogen atom, a straight-chain $C_{1-20}$ hydrocarbon group, a branched or cyclic $C_{3-20}$ hydrocarbon group, or a polymerizable group;

R³ and R⁴ independently represent a hydrogen atom, a straight-chain $C_{1-6}$ alkyl group, or a branched or cyclic $C_{3-6}$ alkyl group; and (ii) an initiator system.

The present invention also provides a process for preparing the acidic polymerizable compound of the formula (Ia), (Ib) or (Ic), which process comprises the steps of:

(a) reacting a mono- or disaccharide with a halogenoalcohol in the presence of a catalytic amount of a Lewis or Brønsted acid for obtaining a halogenoglycoside, (b) substituting of the halogen of the halogenoglycoside with sodium azide for obtaining an azidoglycoside, (c) hydrogenating the azidoglycoside with hydrogen in the presence of a hydrogenation catalyst for obtaining an aminoglycoside, (d) reacting the aminoglycoside with (meth)acryloyl halide for obtaining the corresponding (meth)acrylamide and (e) phosphorylation of the (meth)acrylamide for obtaining an acidic polymerizable compound of the following formula (Ia), (Ib) or (Ic), wherein steps (a) to (e) are carried out as a one-pot process.

Furthermore, the present invention provides a use of an acidic polymerizable compound of the formula (Ia), (Ib) or (Ic) for the preparation of a dental composition.

The present invention is based on the recognition that an acidic polymerizable compound of the formula (Ia), (Ib) or (Ic) provides excellent adhesion to the hard dental tissue, presumably owing to a chelating effect provided by the carbocyclic group. Furthermore, the polymerizable group (R¹) and the optional polymerizable groups R² and Y may be suitably selected in order to provide an acidic polymerizable compound of formula (I) having an advantageous polymerization enthalpy which is comparable to the polymerization enthalpy of (meth)acrylates, (meth)acrylamides and allylic ethers. Besides, the viscosity of the acidic polymerizable compound of formula (I) can be suitably adjusted within the range typically applied in the field of dental compositions. Finally, the acidic polymerizable compound of the following formula (Ia), (Ib) or (Ic) provide desirable mechanical characteristics such as flexural strength. For example, by suitably selecting the polymerizable group R¹ and the optional polymerizable groups R² and Y, and optionally by adding further polymerizable compounds, for example, interpenetrating networks (IPNs) may be formed which provide for an advantageous setting of the mechanical characteristics.

DETAILED DESCRIPTION OF THE PREFERRED EMBODIMENTS

The terms "polymerization" and "polymerizable" relates to the combining or the capability to combine by covalent bonding of a large number of smaller molecules, such as monomers, to form larger molecules, that is, macromolecules or polymers. The monomers may be combined to form only linear macromolecules or they may be combined to form three-dimensional macromolecules, commonly referred to as crosslinked polymers. For example, monofunctional monomers form linear polymers, whereas monomers having at least two functional groups form crosslinked polymers also known as polymer networks. In case of a higher conversion rate of the polymerizable monomer, the amount of multifunctional monomers may be reduced or the leaching problem may be alleviated.

The terms "curing" and "photocuring" mean the polymerization of functional oligomers and monomers, or even polymers, into a crosslinked polymer network. Curing is the polymerization of unsaturated monomers or oligomers in the presence of crosslinking agents.

"Actinic radiation" is any electromagnetic radiation that is capable of producing photochemical action and can have a wavelength of at least 150 nm and up to and including 1250 nm, and typically at least 300 nm and up to and including 750 nm.

The term "photoinitiator" is any chemical compound that forms free radicals when activated, e. g. by exposure to light or interaction with a coinitiator in a photochemical process.

The term "coinitiator" refers to a molecule that produces a chemical change in another molecule such as a photoinitiator in a photochemical process. The coinitiator may be a photoinitiator or an electron donor.

The term "electron donor" as used herein means a compound which is capable of donating electrons in a photochemical process. Suitable examples include organic compounds having heteroatoms with electron lone pairs, for example amine compounds.

The present invention provides a dental composition being polymerizable or copolymerizable by any suitable kind of polymerization, preferably polymerization which can be initiated by a photoinitiator system and/or a redox initiator system.

The dental composition may be a dental material to be used in the oral cavity. Preferably, the present polymerizable dental composition is a dental adhesive composition, a bonding agent, a pit and fissure sealant, a dental desensitizing composition, a pulp capping composition, a dental composite, a flowable dental composite, a dental glass ionomer cement, a dental cement, resin modified glass ionomers, or a dental root canal sealer composition.

Preferably, the dental composition according to the invention is in the form of an aqueous dental composition. The pH value of the aqueous dental composition may be suitably adjusted depending on the components comprised in the dental composition as well as on the intended application. The pH of the dental composition may be adjusted by any means known in the art, e.g. by adding predetermined amounts of one or more acidic compounds to the aqueous dental composition. In this context, the term "acidic compounds" denotes compounds having a $pK_a$ within the range of about −10 to 50. Examples of suitable inorganic acids are sulfuric acid, phosphonic acid, phosphoric acid, hydrochloric acid, nitric acid and the like, which may be used alone or in combination with each other. Examples of suitable organic acids are carboxylic acids which are preferably selected from the group consisting of formic acid, acetic acid, lactic acid, citric acid, itaconic acid, poly(meth)acrylic acid, itaconic acid, maleic acid, polyvinyl phosphonic acid, polyvinyl phosphoric acid, trifluoromethanesulfonic acid, toluenesulfonic acid, methanesulfonic acid, succinic acid, malic acid, tannic acid, toluene sulfonic acid, adipic acid, tartaric acid and ascorbic acid. The set pH-value of the aqueous dental composition may be stabilized by means of a typical chemical buffer system, that is a combination of a weak organic or inorganic acid having a $pK_a$ value at a temperature of 20° C. within the range of about 9 to 50 and its corresponding salt. Alternatively, the buffer system may be in the form of a Norman Goods buffer (Good's buffer) representing organic compounds having a pK$_a$ value at a temperature of 20° C. in a range between about 6 and 8, having biochemical inertness and being suitable for application in a biological system such as the human body. Examples for typical chemical buffer systems are acidic acid/acetate buffer, dihydrogenphosphate/monohydrogen-phosphate buffer or a citric acid/citrate buffer. Examples for Good's buffers are 4-(2-hydroxyethyl)-1-piperazineethanesulfonic acid (HEPES), 2-(N-morpholino)ethanesulfonic acid (MES) or N-cyclohexyl-3-aminopropanesulfonic acid (CAPS). In connection with the term "pH-value" it is noted that the pH-value/system typically relates to aqueous systems wherein water is the main compound, which may for example be present in an amount of about 55 to 90 percent by weight of the liquid phase of the dental composition. The pH-value of the dental composition may be determined by suitable standard means for determining the pH-value of aqueous systems, e.g. by means of a glass electrode.

The Acidic Polymerizable Compound of Formula (I)

The present dental composition comprises (i) an acidic polymerizable compound of formula (Ia), (Ib) or (Ic). The dental composition may comprise one or more acidic polymerizable compounds of formula (Ia), (Ib) or (Ic).

The dental composition of the present invention comprises the acidic polymerizable compounds of formula (Ia), (Ib) or (Ic) n an amount of from 1 to 70 percent by weight based on the total weight of the dental composition. Preferably, the dental composition comprises one or more acidic polymerizable compounds of formula (Ia), (Ib) or (Ic) in an amount of from 10 to 60 percent by weight, most preferably 20 to 60 percent by weight based on the total weight of the entire dental composition.

The amount of an acidic polymerizable compound of the following formula (Ia), (Ib) or (Ic) may be suitably selected in view of the intended application purpose. For example, a dental adhesive may comprise 1 to 70 percent by weight, preferably 20 to 60 percent by weight, based on the total weight of the entire dental composition. A dental primer may comprise 1 to 70 percent by weight, preferably 5 to 25 percent by weight, based on the total weight of the entire dental composition. A pit and fissure sealant may comprise 1 to 70 percent by weight, preferably 5 to 20 percent by weight, based on the total weight of the entire dental composition. A dental glass ionomer cement may comprise 1 to 30 percent by weight, preferably 2 to 10 percent by weight, based on the total weight of the entire dental composition.

The acidic polymerizable compound according to (i) is selected from a generic class of compounds having the following formula (I):

(X)$_m$(Y)$_n$Cyc-Z-L-NR$^1$R$^2$ (I).

In formula (I), Cyc represents a (m+n+1)-valent 4-, 5- or 6-membered carbocyclic group which may contain an oxygen atom in the ring. The carbocyclic group may be saturated or unsaturated. If unsaturated, then the carbocyclic group preferably comprises one or two carbon-carbon double bonds, more preferably one carbon-carbon double bond.

Preferably, Cyc represents a 5- or 6-membered carbocyclic group containing one oxygen atom in the ring, more preferably a saturated 5- or 6-membered carbocyclic group containing one oxygen atom in the ring.

X of formula (I), which may be the same or different, are bonded directly or through a methylene group (—CH$_2$—) to the moiety Cyc independently represent an acidic group selected from a sulfate group, a phosphate group, a sulfonate group, a phosphonate group and a carboxylic acid group (—COOH). The sulfate group is a sulphuric acid group (—SO—(SO$_2$)—OH). The phosphate group may be in the form of a phosphoric acid monoester group (—O—(P=O)(OH)$_2$) or a phosphoric acid diester group (—O—(P=O)(OH)(OR*) wherein R* represents a straight-chain C$_{1-6}$ alkyl group, a branched or cyclic C$_{3-6}$ alkyl group, a straight-chain C$_{2-6}$ alkenyl group or a branched or cyclic C$_{3-6}$ alkenyl group. The sulfonate group is a sulfonic acid group (—(SO$_2$)—OH). The phosphonate group may be in the form of a phosphonic acid group (—(P=O)(OH)$_2$)) or phosphonic acid monoester group (—(P=O)(OH)(OR*)) wherein R* represents a straight-chain C$_{1-6}$ alkyl group, a branched or cyclic C$_{3-6}$ alkyl group, a straight-chain C$_{2-6}$ alkenyl group or a branched or cyclic C$_{3-6}$ alkenyl group.

For R* of the phosphoric acid diester group (—O—(P=O)(OH)(OR*) and the phosphonic acid monoester (—(P=O)(OH)(OR*)), a straight-chain C$_{1-6}$ alkyl group or a branched or cyclic C$_{3-6}$ alkyl group is preferred.

Preferably, group X, which may be the same or different, are bonded directly or through a methylene group (—CH$_2$—) to the moiety Cyc, and independently represent an acidic group selected from a phosphate group, a sulfonate group, a phosphonate group and a carboxylic acid group (—COOH). More preferably, X is a phosphate group, most preferably a phosphoric acid monoester group (—O—(P=O)(OH)$_2$), which may be bonded directly or through a methylene group to the moiety Cyc.

X is present in formula (I) m times, wherein m represents an integer of from 1 to 5.

Formula (I) may optionally contain Y representing a hydrogen atom, a methyl group, a hydroxyl group, an amino group, a polymerizable group, a thiol group or an amide group. Alternatively, two optional groups Y present at adjacent carbon atoms of the carbocyclic group Cyc form together with the carbon atoms to which they are bonded a cyclic acetal, phosphate or oxazoline. Each group Y is bonded directly or through a methylene group to the moiety Cyc.

Preferably, the optional group Y is a hydrogen atom, a methyl group, a hydroxyl group, an amino group or an amide group, or alternatively, two optional groups Y present at adjacent carbon atoms of the carbocyclic group Cyc form together with the carbon atoms to which they are bonded a cyclic acetal or phosphate, wherein each group Y is bonded directly or through a methylene group to the moiety Cyc. More preferably, the optional group Y is a hydrogen atom, a methyl group, a hydroxyl group, an amino group or an amide group, or alternatively, two optional groups Y present at adjacent carbon atoms of the carbocyclic group Cyc form together with the carbon atoms to which they are bonded a cyclic acetal or phosphate, wherein each group Y is bonded directly or through a methylene group to the moiety Cyc. Even more preferably, the optional group Y is a hydrogen atom, a methyl group, a hydroxyl group, a hydroxymethyl group, an amide group or a methyleneamide group, or alternatively, two optional groups Y present at adjacent carbon atoms of the carbocyclic group Cyc form together with the carbon atoms to which they are bonded a cyclic acetal, wherein each group Y is bonded directly to the moiety Cyc. Yet even more preferably, the optional group Y is an amide group or a methylene amide group bonded directly to the moiety Cyc. Most preferably, the optional group Y is an amide group bonded directly to the moiety Cyc.

For group Y, the amide group is not specifically limited. However, it is preferred for Y that the amide group is in the form of —CO—NH—$R^{\#}$ or —NH—CO—$R^{\#}$, wherein $R^{\#}$ represents a hydrocarbon group. More preferably, Y in the form of an amide group is —NH—CO—$R^{\#}$, wherein $R^{\#}$ is a straight-chain $C_{1-6}$ alkyl group or a branched or cyclic $C_{3-6}$ alkyl group. Even more preferably, Y in the form of an amide group —NH—CO—$R^{\#}$, wherein $R^{\#}$ is a straight-chain $C_{1-6}$ alkyl group or a branched $C_{3-6}$ alkyl group, and most preferably the amide —NH—CO—$CH_2$—$CH_3$, that is N-Acetyl.

The optional moiety Y is present in formula (I) n times, wherein n represents an integer of 0 to 3, and preferably n is 1.

Most preferably, Y is an amide group and n is 1.

For Z of formula (I), it may be selected between alternative features α) or β). If Z is according to α), then formula (I) contains only one carbocyclic group Cyc. If Z is according to β), then formula (I) contains the two carbocyclic groups Cyc and Cyc*. For example, when the carbocyclic groups Cyc and Cyc* represent saccharides, according to α), formula (I) represents a monosaccharide compound, while according to β), formula (I) represents a disaccharide compound.

According to α), group Z represents a single bond, a carbamate group (—O—(C=O)—NH—), a thiocarbamate group (—O—(C=S)—NH— or —S—(C=O)—NH—), a dithiocarbamate group (—S—(C=S)—NH—), a urea group (—NH—(C=O)—NH—), a thiourea group (—NH—(C=S)—NH—), an oxygen atom, a sulfur atom, or a group NR'. In group NR', R' represents a hydrogen atom, a straight-chain $C_{1-6}$ alkyl group, or a branched or cyclic $C_{3-6}$ alkyl group which may be substituted with a phosphonate group. Group Z is bonded directly or through a methylene group to the moiety Cyc.

Preferably, Z according to α) represents a carbamate group, a thiocarbamate group, a dithiocarbamate group group, an oxygen atom or a sulphur atom, more preferably a carbamate group or an oxygen atom. Most preferably, Z according to α) represents an oxygen atom.

Alternatively, according to β), Z may represent a group —O—(X*)$_m$*(Y*)$_n$*Cyc*-Z*- wherein X*, Y*, Cyc*, Z*, m* and n* have the same meaning as defined for X, Y, Cyc, Z according to α), m and n and are independently selected therefrom. According to the aforementioned "same meaning", in group —O—(X*)$_m$*(Y*)$_n$*Cyc*-Z*- of Z according to β), X*, Y* and Z* are respectively bonded directly or through a methylene group to the moiety Cyc*.

For Z according to both α) and β), the carbamate group, the thiocarbamate group and the dithiocarbamate group may be bonded to the moiety Cyc or Cyc* via their pendant oxygen or sulphur atom. Alternatively, these groups may be bonded to the moiety Cyc or Cyc* via their nitrogen atom.

L represents a divalent linker group.

For L, the linker group may be a hydrocarbon group which may be aliphatic and/or aromatic, preferably aliphatic, and preferably has 1 to 45 carbon atoms. The aliphatic hydrocarbon group may be saturated or unsaturated. The hydrocarbon group may be substituted with 1 to 6 $C_{1-4}$ alkyl groups. Specific examples of the alkyl groups are methyl, ethyl, n-propyl, i-propyl, n-butyl, i-butyl or tert.-butyl. In a preferred embodiment, for L, the hydrocarbon group of the linker group may contain 1 to 20 heteroatoms selected from oxygen, nitrogen and sulphur. The oxygen atoms, nitrogen atoms and sulphur atoms in the hydrocarbon group may be in the form of ether or thioether bonds, amine bonds, keto or sulfoxide groups, carboxylic acid or ester groups, amide groups, sulfonic acid or ester groups, hydroxyl groups and thiol or thioester groups.

Preferably, L is a divalent $C_{1-20}$ hydrocarbon which may contain one or more heteroatoms selected from the group of an oxygen atom, a sulfur atom, and a nitrogen atom. More preferably, L is an aliphatic group in the form of a linear $C_1$ to $C_{20}$ or branched $C_3$ to $C_{20}$ alkylene group, linear $C_2$ to $C_{20}$ and branched $C_3$ to $C_{20}$ alkenylene group, $C_3$ to $C_{20}$ cycloalkylene or cycloalkenylene group which may contain 1 to 20 heteroatoms selected from oxygen, nitrogen and sulphur, which heteroatoms may be in the form described above.

According to one aspect of the invention, L is a group of the following formula (II)

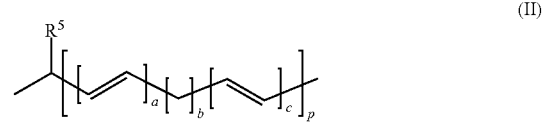

(II)

wherein $R^5$ is a hydrogen atom or a hydrocarbon group, a, b and c, which may be the same or different, are integers of from 0 to 3, and p is 0, 1 or 2. Preferably, $R^5$ is a hydrogen atom or a straight-chain $C_{1-6}$ alkyl group, a branched or cyclic $C_{3-6}$ alkyl group, a straight-chain $C_{2-6}$ alkenyl group or a branched or cyclic $C_{3-6}$ alkenyl group. More preferably, $R^5$ is a hydrogen atom, a straight-chain $C_{1-6}$ alkyl group or a branched or cyclic $C_{3-6}$ alkyl group, and most preferably, $R^5$ is a hydrogen atom.

In formula (II), preferably, p is 0 or 1. Further, it is preferred that b is 0. For a and c, it is preferred that a or c is 0. Preferably, in formula (II) a is 1, b is 0 or 1 and c is 0 to 3. More preferably, a is 1, b is 0 or 1 and c is 0 or 1, and most preferably a=1, b=c=0.

According to another aspect of the invention, L may be an alkylene(polyoxyalkylene) group or a $C_{2-6}$ alkenylene group. The alkylene(polyoxyalkylene) for L is not particularly limited, but preferably, it is a $C_{2-6}$ alkenylene-(O—$C_{2-6}$ alkylene)$_k$ wherein k is 1 to 20. For the $C_{2-6}$ alkenylene group, which may be bonded to Z or N of formula (I), it is preferred that the carbon-carbon double bond is located between the second and third carbon atom located adjacent to Z or N of formula (I). Preferably, the alkylene(polyoxyalkylene) is ethylene(polyoxyethylene) wherein k is 1 to 10.

$R^1$ of formula (I) represents a polymerizable group.

$R^2$ of formula (I) represents a hydrogen atom, a straight-chain $C_{1-20}$ hydrocarbon group, a branched or cyclic $C_{3-20}$ hydrocarbon group, or a polymerizable group. Preferably, $R^2$ of formula (I) represents a hydrogen atom, a straight-chain $C_{1-14}$ hydrocarbon group, a branched or cyclic $C_{3-14}$ hydrocarbon group, or a polymerizable group. More preferably, $R^2$ of formula (I) represents a hydrogen atom, a straight-chain $C_{1-6}$ hydrocarbon group, a branched or cyclic $C_{3-6}$ hydrocarbon group, or a polymerizable group. The term "hydrocarbon group" as used herein in connection with $R^2$ means an alkyl or alkenyl group.

For $R^1$, $R^2$ and Y, the polymerizable group is not particularly limited as long as it is susceptible to polymerization, preferably polymerization induced by a photoinitiator system, a redox initiator system or a dual cure initiator system. It is preferred that the polymerizable group is a radically polymerizable carbon-carbon double bond or a cationically polymerizable group. Radically polymerizable carbon-carbon double bonds may be selected from (meth)acryloyl group(s) and a (meth)acrylamide group(s), preferably (meth)acryloyl group(s). Cationically polymerizable group(s) may be selected from epoxide groups, oxetane groups, vinyl ether groups, aziridine groups, and azetidine groups. Preferably, for $R^1$, the polymerizable group is a (meth)acryloyl group or a (meth)acrylamide group, for $R^2$, the optional polymerizable group represents an alkenyl group such as a vinyl or allyl group, and for at least one Y, the optional polymerizable group represents an epoxide group, oxetane group or a vinyl ether group. Most preferably, for $R^1$, the polymerizable group is a (meth)acryloyl group, for $R^2$, the optional polymerizable group represents an allyl group, and for one Y, the optional polymerizable group represents a a vinyl ether group.

Most preferably, $R^1$ represents a (meth)acryloyl group.

Most preferably, $R^2$ represents a hydrogen atom or an allyl group.

Preferably, the acidic polymerizable compound of formula (I) represent a glycoside, that is the moiety $(X)_m(Y)_n$Cyc-Z- represents a mono- or disaccharide, which is linked to the divalent linker group L via a glycosidic bond provided by Z.

The glycoside is in the form of a monosaccharide glycoside of formula (Ia) or (Ib) or a disaccharide glycoside of formula (Ic):

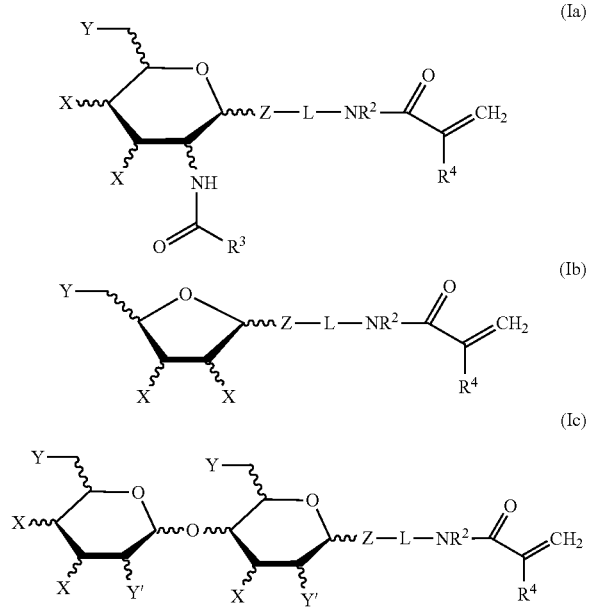

wherein X, Y, Z, L, and $R^2$ are as defined above, Y' represents an OH or amide group —NH—(C=O)—$R^3$, and $R^3$ and $R^4$ independently represent a hydrogen atom, a straight-chain $C_{1-6}$ alkyl group, or a branched or cyclic $C_{3-6}$ alkyl group.

In formula (Ia), (Ib) and (Ic), the jagged lines indicate that the respective substituent Y—CH$_2$—, X, Y' and Z may be located above (up-position) or below (down-position) the plane of the ring of the carbocyclic group Cyc illustrated as a Haworth projection.

Preferably, in formula (Ia), (Ib) and (Ic), Z (or Z*) represents a single bond, an oxygen atom, a sulphur atom or a group —NR' wherein R' is defined as above. Most preferably, Z (or Z*) represents an oxygen atom.

Preferably, compound of formula (Ia) and (Ib) are selected from a glucoside, a fructoside, a glucuronide, a mannoside, a galactoside, a riboside, an alloside, an altroside, a guloside, an idoside, a taloside, a rhamnoside, a xyloside, a psicoside, a lyxoside, an arabinoside, a sorboside, a tagatoside, or a deoxy sugar derivative thereof.

Additionally, compound of formula (Ib) may preferably be selected from a a ribuloside, a xyluloside, an erythreoside, a threoside, or a deoxy sugar derivative thereof.

Preferably, compound of formula (Ic) is selected from a lactoside, a maltoside, a chitobioside, or a deoxy sugar derivative thereof.

Preferably, the acidic polymerizable compound of formula (Ia), (Ib) or (Ic) is a crosslinker. The term "crosslinker" as used herein in connection with the acidic polymerizable compound of formula (Ia), (Ib) or (Ic) means any compound having two or more polymerizable groups, wherein at least one of these polymerizable groups is $R^1$ representing a polymerizable group as defined above, and optionally $R^2$ and/or Y representing a polymerizable group which may be bonded directly or through a methylene group to the moiety Cyc and optionally Cyc*. If the acidic polymerizable compound of the following formula (Ia), (Ib) or (Ic) is a crosslinker, then besides of the aforementioned polymerizable groups, X representing an acidic group or Y representing a hydroxyl group, an amino group or a thiol group, which may be bonded directly or through a methylene group to the moiety Cyc, may also serve as polymerizable groups. These groups X and Y may react or polymerize with themselves or other components of the dental composition by means of (poly)addition or (poly)condensation reactions.

Process for Preparing the Acidic Polymerizable Compound of Formula (I)

The acidic polymerizable compound of formula (Ia), (Ib) or (Ic) is not limited by a specific process for preparation, but may be provided by any process suitable for preparation.

However, preferably, the acidic polymerizable compound of formula (Ia), (Ib) or (Ic) is obtained by a process comprising the steps of:
(a) reacting a mono- or disaccharide with a halogenoalcohol in the presence of a catalytic amount of a Lewis or Brønsted acid for obtaining a halogenoglycoside,
(b) substituting of the halogen of the halogenoglycoside with sodium azide for obtaining an azidoglycoside,
(c) hydrogenating the azidoglycoside with hydrogen in the presence of a hydrogenation catalyst for obtaining an aminoglycoside,
(d) reacting the aminoglycoside with (meth)acryloyl halide for obtaining the corresponding (meth)acylamide and
(e) phosphorylation of the (meth)acrylamide for obtaining an acidic polymerizable compound of formula (Ia), (Ib) or (Ic).

Specifically, the aforementioned steps (a) to (e) are as follows:
(a) reacting a mono- or disaccharide of the following formula (III)

wherein Cyc has the same meaning as defined above for formula (I), $Y^\#$ has the same meaning as Y defined above for compound of formula (I), $n^\#$ represents an integer from 1 to 8, and $Z^\#$ is a carbamidacid group (—NH—CO—OH), a thiocarbamidacid (—NH—CS—OH) group, a dithiocarbamidacid group (—NH—CS—SH) group, a hydroxyl group or a thioalcohol group (—SH), preferably $Z^{\#}$ is a hydroxyl group, with a halogenoalcohol of the following formula (IV)

Hal-L-Alc (IV)

wherein Hal is a halogen preferably selected from chlorine and bromine, L has the same meaning as defined above for formula (I), and Alc is a hydroxyl or thioalcohol group, preferably a hydroxyl group, in the presence of a catalytic amount of a Lewis or Brønsted acid for obtaining a halogenoglycoside of the following formula (V)

$(Y^{\#})_{n\#}$Cyc-Z'-L-Hal (V)

wherein Cyc, $Y^{\#}$ and $n^{\#}$ have the same meaning as defined above for formula (III), Hal has the same meaning as defined above for formula (VI), and Z' is a carbamate group (—NH—CO—O—), a thiocarbamate (—NH—CS—O—) group, a dithiocarbamate group (—NH—CS—S—) group, an oxygen atom (—O—) or a sulphur atom (—S—), (b) substituting the halogenide of the halogenoglycoside of formula (V) with sodium azide for obtaining an azidoglycoside of the following formula (VI)

$(Y^{\#})_{n\#}$CyC-Z'-L-N$_3$ (VI)

wherein Cyc, $Y^{\#}$, $n^{\#}$ and Z' have the same meaning as defined above for formula (V), (c) hydrogenating the azidoglycoside of formula (VI) with hydrogen in the presence of a hydrogenation catalyst for obtaining an aminoglycoside of the following formula (VII),

$(Y^{\#})_{n\#}$Cyc-Z'-L-NH$_2$ (VII)

wherein Cyc, $Y^{\#}$, $n^{\#}$ and Z' have the same meaning as defined above for formula (V), (d) reacting the aminoglycoside of formula (VII) with (meth)acryloyl halide for obtaining the corresponding (meth)acylamide of the following formula (VIII)

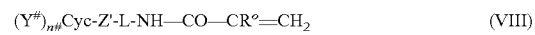

$(Y^{\#})_{n\#}$Cyc-Z'-L-NH—CO—CR$^o$=CH$_2$ (VIII)

wherein Cyc, $Y^{\#}$, $n^{\#}$ and Z' have the same meaning as defined above for formula (V), and $R^o$ is a hydrogen atom or a methyl group, and (e) phosphorylation of the (meth)acrylamide of formula (VIII) for obtaining an acidic polymerizable compound of formula (I).

By way of example, in Scheme 1, the process comprising steps (a) to (e) is depicted for N-acetylglucosamin (GlcNAc) as compound of formula (III):

Scheme 1 Process comprising steps (a) to (e) for the synthesis of compound of formula (I) wherein
$(X)_m(Y)_n$Cyc—Z— is the O-glycoside of GlcNAc, $R_1$ = acryloyl and $R_2$ = H

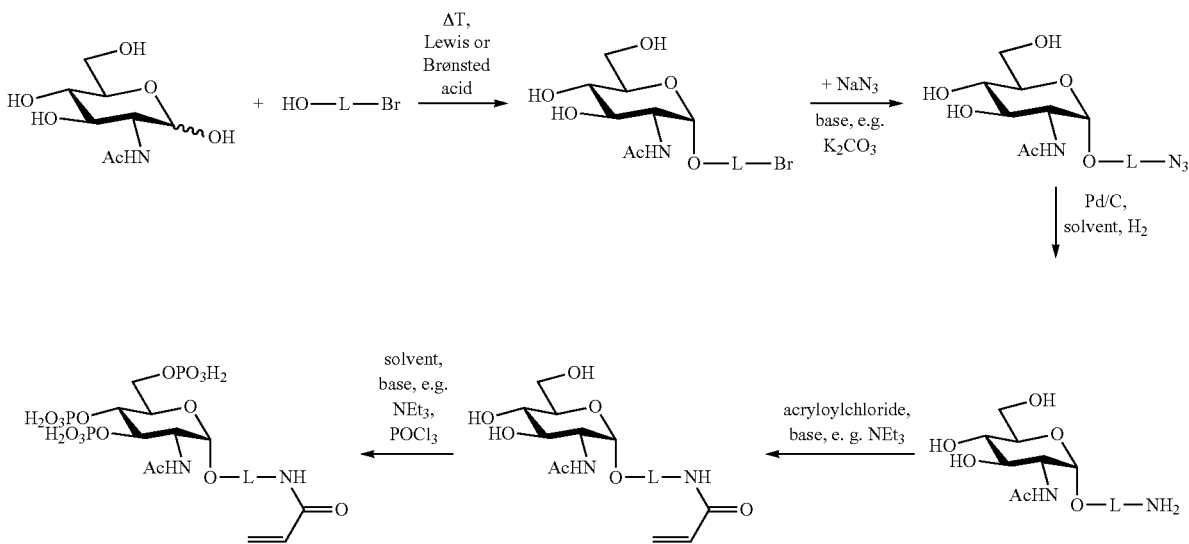

Preferably, a process comprising the steps (a) to (e) as defined above is carried out as a one-pot process.

According to an alternative preferred embodiment, the acidic polymerizable compound of formula (I) is obtainable by a process comprising the steps of:

(I-1) reacting a mono- or disaccharide with an azidoalcohol in the presence of a catalytic amount of a Lewis or Brønsted acid for obtaining an azidoglycoside, followed by hydrogenating the obtained azidoglycoside with hydrogen in the presence of a hydrogenation catalyst for obtaining an aminoglycoside, or (I-2) reacting a mono- or disaccharide with a halogenoalcohol in the presence of a catalytic amount of a Lewis or Brønsted acid for obtaining a halogenoglycoside, and substituting the halogen of the halogenoglycoside with an alkylamine or alkenylamine for obtaining an alkyl- or alkenyl-aminoglycoside or alkenylaminoglycoside;

(I-3) reacting a mono- or disaccharide with an N-alkyl- or N-alkenylalcohol in the presence of a catalytic amount of a Lewis or Brønsted acid for obtaining an alkyl- or alkenylaminoglycoside (II) reacting the aminoglycoside obtained in step (i-1) or the alkyl- or alkenyl-aminoglycoside obtained in step (I-2) or (I-3) with (meth)acryloyl halide for obtaining the corresponding (meth)acrylamide and (III) phosphorylation of the (meth)acrylamide for obtaining an acidic polymerizable compound of formula (I).

Specifically, the aforementioned steps (I-1), (I-2) or (I-3) to (III) are as follows:

(I-1) reacting the mono- or disaccharide of formula (III) as defined above with an azidoalcohol of the following formula (IX)

$$N_3\text{-L-Alc} \qquad (IX)$$

wherein L has the same meaning as defined above for formula (I), and Alc is a hydroxyl group or a thioalcohol group, preferably a hydroxyl group, in the presence of a catalytic amount of a Lewis or Brønsted acid for obtaining an azidoglycoside of the following formula (VI)

$$(Y^{\#})_{n\#}\text{Cyc-Z'-L-}N_3 \qquad (VI)$$

wherein Cyc, $Y^{\#}$, $n^{\#}$ and Z' have the same meaning as defined above for formula (V), followed by hydrogenating the obtained azidoglycoside of formula (VI) with hydrogen in the presence of a hydrogenation catalyst for obtaining an aminoglycoside of the above formula (VII), or (I-2) reacting a mono- or disaccharide of formula (III) as defined above with a halogenoalcohol of the above defined formula (IV) in the presence of a catalytic amount of a Lewis or Brønsted acid for obtaining a halogenoglycoside of the above formula (V), and substituting the halogen of said halogenoglycoside with an alkylamine or alkenylamine for obtaining an alkyl- or alkenyl-aminoglycoside of the following formula (X)

$$(Y^{\#})_{n\#}\text{Cyc-Z'-L-NH-}R^{2'} \qquad (X)$$

wherein Cyc, $Y^{\#}$, $n^{\#}$ and L' have the same meaning as defined above for formula (V), and $R^{2'}$ is an alkyl or alkenyl group, preferably a linear $C_{1-4}$ or branched C3 or C4 alkyl group or a linear $C_{2-4}$ or branche C3 or C4 alkyl group, more preferably a methyl group, an ethyl group or an allyl group, most preferably an allyl group, (I-3) reacting a mono- or disaccharide of formula (III) as defined above with an N-alkyl- or N-alkenylalcohol of formula (XI)

$$\text{Alc-L-NH-}R^{2'} \qquad (XI),$$

wherein L is defined as above for formula (I), $R^{2'}$ is an alkyl- or alkenyl group as defined above for formula (X), and Alc is a hydroxyl or thioalcohol group, preferably a hydroxyl group, in the presence of a catalytic amount of a Lewis or Brønsted acid for obtaining an alkyl- or alkenyl-aminoglycoside of the above formula (X)

(II) reacting the aminoglycoside of formula (VII) obtained in step (I-1) or the alkyl- or alkenyl-aminoglycoside of formula (XI) obtained in step (I-2) or (I-3) with (meth) acryloyl halide for obtaining the corresponding (meth) acrylamide of the above formula (VIII) or the alkyl- or alkenyl-(meth)acrylamide of the following formula (XII)

$$(Y^{\#})_{n\#}\text{Cyc-Z'-L-N}R^{2'}\text{-CO-C}R^{o}\text{=CH}_2 \qquad (XII)$$

wherein Cyc, $Y^{\#}$, $n^{\#}$ and Z' have the same meaning as defined above for formula (V), $R^{2'}$ is an alkyl or alkenyl group as defined above for formula (X), and $R^{o}$ is a hydrogen atom or a methyl group, and (III) phosphorylation of the (meth)acrylamide of formula (VIII) or (XII) for obtaining an acidic polymerizable compound of formula (I).

In the above described processes, in the acidic polymerizable compound of formula (Ia), (Ib) or (Ic), the specific selection Z' for Z is a group consisting of a carbamate group (—NH—CO—O—), a thiocarbamate (—NH—CS—O—) group, a dithiocarbamate group (—NH—CS—S—) group, an amide group (—NH—CO—), an oxygen atom (—O—) and a sulphur atom (—S—). This specific selection Z' is due to the reacting with an alcohol in the form of a compound of formula (IV), (IX) or (XI) in the above described processes.

However, it is readily understood that besides of the specific selection Z', the remaining components of the group of Z can also be readily prepared. For example, Z in the form of a single bond is obtainable by reacting a mono- or disaccharide having an aldehyde group with e.g. a phosphonate compound of formula $(R^{\blacktriangledown}O)_2P$-L-NProt, wherein $R^{\blacktriangledown}$ is an alkyl or aryl group, and NProt is a protected amino group, in the presence of a strong Brønsted base such as sodium hydride (NaH) by means of a Horner-Wadsworth-Emmons (HWE) reaction. Then, in the resulting mono- or disaccharide, the protected amino group NProt is deprotected to obtain a terminal amino group —NH$_2$. The deprotected resulting mono- or disaccharide can be analogously subjected to the above described steps (II) and (III) to obtain an acidic polymerizable compound of formula (Ia), (Ib) or (Ic).

Furthermore, a an acidic polymerizable compound of formula (I) wherein group Z is in the form of a urea group, a thiourea group or a group N—R', is obtainable by reacting a starting material in the form of a mono- or disaccharide having an urea group, a thiourea group or an amino group (—NH$_2$) with a halogenide compound of the formula X-L-NProt wherein X is a halogen atom, preferably a bromo, chloro or iodo atom, and NProt is a protected amino group. The halogen atom will be substituted by the amino group (—NH$_2$) or the terminal amino group of the urea group or the thiourea group of the mono- or disaccharide. Then, in the resulting mono- or disaccharide, the protected amino group NProt is deprotected to obtain a terminal amino group —NH$_2$. The deprotected resulting mono- or disaccharide can be analogously subjected to the above described steps (II) and (III) to obtain an acidic polymerizable compound of formula (Ia), (Ib) or (Ic).

The above mentioned protecting group Prot for protecting an amino group is not particularly limited as long as it is not cleavable under basic conditions, and may be any conventional amino protecting group, for example, described in P. G. M. Wuts and T. W. Greene, Greene's Protective Groups in Organic Synthesis, 4th Edition, John Wiley and Sons Inc., 2007.

In the following, the conditions for carrying out steps (a) to (e) and (I-1), (I-2) or (I-3) to (III) of the aforementioned processes are described.

In steps (a), (I-1), (I-2) and (I-3), the Lewis or Brønsted acid is not specifically limited. Any Lewis acid, that is a compound capable of donating electrons, and any Brønsted acid, that is a compound capable of donating a proton, may be applied in these steps. Preferably, a Lewis acid is applied in steps (a), (I-1), (I-2) and (I-3), more preferably a Lewis acid selected from the group consisting of trihalides of trifluorides, trichlorides, tribromides or triiodides of B, Fe, Al, Bi, Cr, and ZnCl$_2$, which tri- and dihalides may complexed with a solvent such a diethyleter whereby e.g. an etherate is formed, and tri-trifluoromethanesulfonates (triflate, OTf) or tri-trifluoromethansulfonimidates (triflimidates, TFSI) of B, Fe, Al, Bi, Cr, Sc, In, Ga, Nd, and trimethylsilyl trifluoromethanesulfonate (TMSOTf). Most preferably, in step (a), the Lewis acid is boron trifluoride etherate ($BF_3.OEt_2$) or trimethylsilyl trifluoromethanesulfonate (TMSOTf).

In steps (a), (I-1), (I-2) and (I-3), the Lewis or Brønsted acid may be applied in any catalytic amount suitable for reacting the mono- or disaccharide with the halogenoalcohol of formula (IV), the azidoalcohol of formula (IX), or the N-alkyl- or N-alkenylalcohol of formula (XI), in order to obtain a halogenoglycoside of formula (V), an azidoglycoside of formula (VI) or an N-alkyl- or N-alkenylalcohol of formula (XI). Preferably the catalytic amount of Lewis or Brønsted acid is up to 30 mol % relative to the mono- or disaccharide of formula (III), more preferably 3 to 20 mol %, most preferably 5 to 10 mol %.

In steps (a), (I-1), (I-2) and (I-3), the halogenoalcohol of formula (IV), the azidoalcohol of formula (IX), or the N-alkyl- or N-alkenylalcohol of formula (XI) is applied in a hyperstoichiometric amount relative to the mono- or disaccharide of formula (III), preferably in an amount of at least 4 equivalents relative to the mono- or disaccharide of formula (III), more preferably 6 to 25 equivalents, most preferably 8 to 6 equivalents.

Steps (a), (I-1), (I-2) and (I-3) are preferably carried out at an elevated temperature which typically is around the boiling point of the halogenoalcohol of formula (IV), the azidoalcohol of formula (IX), or the N-alkyl- or N-alkenyl-alcohol of formula (XI). More preferably, steps (a), (I-1), (I-2) and (I-3) are carried out at a temperature of 60 to 120° C., most preferably 70 to 90° C.

In steps (a), (I-1), (I-2) and (I-3), the products in the form of the halogenoglycoside of formula (V), the azidoglycoside of formula (VI) and the alkyl- or alkenyl-aminoglycoside of formula (X) may be purified by any suitable purification method, most preferably by column chromatography.

In step (I-3), the N-alkyl or N-alkenylalcohol of formula (XI) can be readily prepared from commercially available starting materials. For example, the N-alkyl or N-alkenyl-alcohol of formula (XI) may be prepared by reacting a halogenoalcohol of formula (IV) with an alkyl- or alkenyl-amine $R^{2'}$—$NH_2$ of formula (XIII), wherein $R^{2'}$ is an alkyl- or alkenyl group as defined above for formula (X).

In steps (b) and (I-2), the reaction conditions for substituting the halogenide of the halogenoglycoside of formula (V) with sodium azide may be suitably selected. Typically, these reaction steps are carried out at elevated temperature, preferably at a temperature of 80 to 120° C. Preferably, sodium azide is applied in a hyperstochiometric amount relative to the halogenoglycoside of formula (V), more preferably in an amount of at least 1.2 equivalents relative to the halogenoglycoside of formula (V), most preferably in an amount of 1.5 to 2.5 equivalents.

In steps (c) and (I-1), any suitable hydrogenation catalyst may be applied. Preferably, the hydrogenation catalyst is selected from the group of heterogenous catalysts consisting of Pd or Pt in elemental form or in the form of an oxide or hydroxide, optionally on a support such as carbon or charcoal, Raney Nickel (representing a Ni—Al alloy) or Lindlar catalyst (Pd deposited on $CaCO_3$ and poisoned by lead or sulfur). Preferably, the hydrogenation catalyst is Pd in elemental form or in the form of an oxide or hydroxide, optionally on a support such as carbon or charcoal. Most preferably, the hydrogenation catalyst is Pd in elemental form on a charcoal support (Pd/C), wherein the amount of elemental Pd is preferably between 4 to 12% by weight relative to the total weight of Pd/C.

In steps (c) and (I-1), the hydrogenation catalyst is preferably applied in an amount of up to 20% by weight relative to the azidoglycoside of formula (VI), more preferably 2 to 15% by weight, most preferably 4 to 10% by weight.

Steps (c) and (I-1) are preferably carried out at a temperature of 0 to 40° C., more preferably 10 to 30° C., most preferably 15 to 25° C.

In steps (c) and (I-1), a solvent is typically applied. Preferably, the solvent is an alkyl alcohol or an alkyl ether, more preferably a $C_{1-6}$ alkyl alcohol, a $C_{1-6}$ dialkyl ether or a cyclic alkylether in the form of tetrahydrofuran (THF) or tetrahydropyran, most preferably ethanol.

In steps (c) and (I-1), the products in the form of the aminoglycoside of formula (VII) may be used without further purification in the following step, provided that there is full conversion of the azidoglycoside of formula (VI) to the aminoglycoside of formula (VII). However, before carrying out the following step, preferably the solvent and the hydrogenation catalyst are removed.

In steps (d) and (II), the (meth)acryloyl halide applied may be a (meth)acryloyl fluoride, chloride, bromide or iodide. Preferably, the (meth)acryloyl halide is (meth)acryloyl chloride or bromide, most preferably (meth)acryloyl chloride.

In steps (d) and (II), a Brønsted base is typically applied, preferably an organic Brønsted base, more preferably a tertiary alkylamine, even more preferably a tri-$C_{1-4}$-alkylamine, most preferably triethyl amine or diisopropylethylamine. The Brønsted base is preferably applied in a hyperstoichiometric amount relative to the aminoglycoside of formula (VII) or the alkyl- or alkenyl-aminoglycoside of formula (X), more preferably in an amount of 1.5 to 4 equivalents relative to the aminoglycoside of formula (VII) or the alkyl- or alkenyl-aminoglycoside of formula (X), most preferably in an amount of 2 to 2.5 equivalents.

In steps (d) and (II), the product in the form of the (meth)acrylamide of formula (VII) or the the alky- or alkenyl-(meth)acrylamide of formula (XII) may be purified by any suitable purification method, most preferably by an aqueous workup.

In step (e) and (III), group X of formula (I) representing a phosphonate group is formed by means of phosphorylation. For phosphorylation, a phosphorylation agent is applied. Preferably, phosphorus oxychloride ($POCl_3$) is applied as the phosphorylation agent.

Preferably, at least one equivalent of phosphorus oxychloride is applied per Y in the form of a hydroxyl group attached to the carbocyclic group Cyc.

In steps (e) and (III), a solvent is typically applied. Preferably, the solvent is an alkyl ether, more preferably a $C_{1-6}$ dialkyl ether or a cyclic alkylether in the form of tetrahydrofuran (THF) or tetrahydropyran, most preferably THF.

In steps (e) and (III), a Brønsted base is typically applied, wherein the kind and amount of Brønsted base is the same as defined above for steps (d) and (II), and is independently selected therefrom.

In steps (e) and (III), the product in the form of compound of formula (I) may be purified by any suitable purification method. Most preferably, the reaction mixture of steps (e) and (III) is washed with brine, then dried, and finally the solvent is removed to yield the desired compound of formula (I). The product may be further purified by column chromatography whereby reversed-phase methods such as reversed phase silica gel in methanol:acetonitrile (1:1) may be mentioned.

In all process steps (a) to (e) and (I-1), (I-2), (I-3) to (III), suitable reaction times can be determined by conversion control, for example by thin layer chromatography, gas chromatography or NMR.

By way of example, in Scheme 2, the process comprising steps (I-1), (II) and (III) is depicted wherein N-acetylglucosamin (GlcNAc) is used as compound of formula (III):

Scheme 2 Process comprising steps (I-1), (II) and (III) for the synthesis of compound of formula (I) wherein $(X)_m(Y)_n\text{Cyc}—Z—$ is the O-glycoside of GlcNAc, $R_1$ = acryloyl and $R_2$ = H

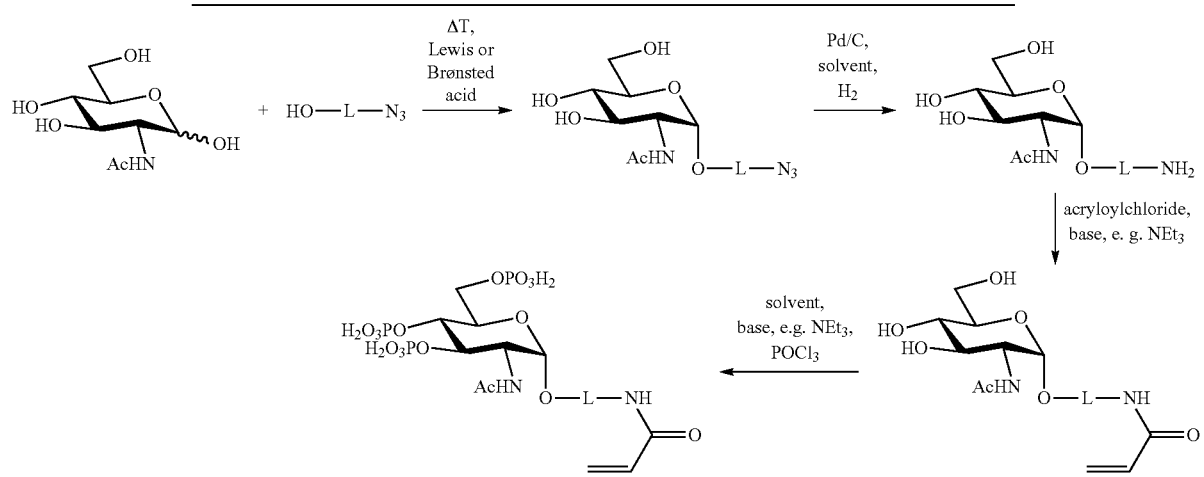

Furthermore, by way of example, in Scheme 3, the process comprising steps (I-2) or (I-3), (II) and (III) is depicted wherein N-acetylglucosamin (GlcNAc) is used as compound of formula (III):

Scheme 3 Process comprising steps (I-2) or (I-3), (II) and (III) for the synthesis of compound of formula (I) wherein $(X)_m(Y)_n\text{Cyc}—Z—$ is the O-glycoside of GlcNAc, $R_1$ = acryloyl and $R_2$ = allyl

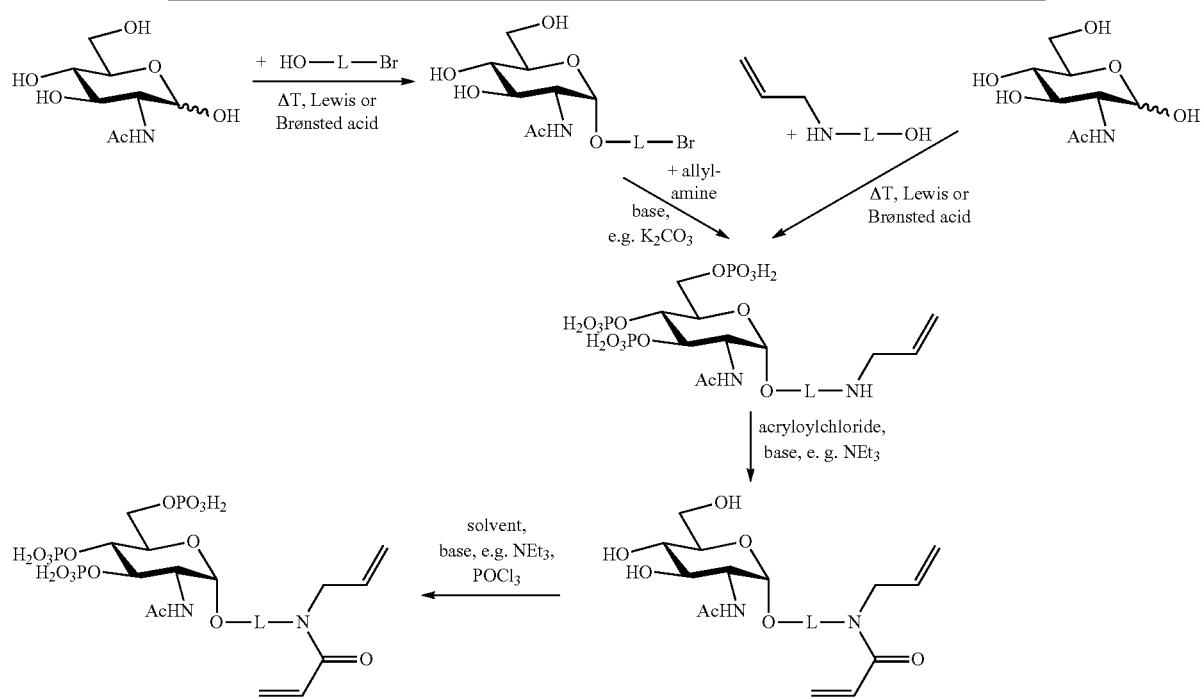

The acidic polymerizable compound of formula (Ia), (Ib) or (Ic), wherein Z is other than an oxygen atom may be prepared according to synthetic methods known in the art. For example, thioglycosides wherein Z is a sulfur atom may be prepared according to Fügedi, P. et al., J. Glycoconjugate (1987) 4:97-108 or Codée, J. D. C. et al., Chem. Soc. Rev., 2005, 34, 769-782. N-Aryl glycosides may be prepared according to Fosso, M. Y. et al., Journal of Carbohydrate Chemistry, 31: 603-619, 2012. β-N-glycosides may be prepared according to Zheng, J. et al., Angew. Chem. Int. Ed. Engl. 2013, 52(23): 6068-6071 or Smith, K. J. J. org. Chem. 1981, 46, 3158-3160.

The Initiator System (ii)

The dental composition according to the present invention comprises an initiator system according to (ii). As a initiator system according to (ii), any compound or system capable of initiating the polymerization of the acidic polymerizable compound of formula (I) according to the present invention may be used. The initiator system according to (ii) may be a photoinitiator system, a redox initiator system or a dual cure initiator system.

The term "dual cure initiator system" means an initiator system that contains a photoinitiator system and a redox initiator system.

For example, a suitable photoinitiator system may be in the form of a binary or tertiary system. A binary system may include a photoinitiator and an electron donor compound, and a tertiary system may include an iodonium, sulfonium or phosphonium salt, a photoinitiator, and an electron donor compound, as for example described in U.S. Pat. No. 5,545,676.

Suitable photoinitiators for the initiator system (ii) are monoketones and diketones that absorb some light within a range of about 400 nm to about 520 nm (preferably, about 450 nm to about 500 nm). Particularly suitable compounds include alpha diketones that have some light absorption within a range of about 400 nm to about 520 nm (even more preferably, about 450 to about 500 nm). Examples include camphor quinone, benzil, furil, 3,3,6,6-tetramethylcyclohexanedione, phenanthraquinone, 1-phenyl-1,2-propanedione and other 1-aryl-2-alkyl-1,2-ethanediones, and cyclic alpha diketones. Suitable electron donor compounds include substituted amines, e.g., ethyl dimethylaminobenzoate or dimethylamino benzonitrile.

A suitable photoinitiator system may also include phosphine oxides typically having a functional wavelength range of about 380 nm to about 1200 nm. Examples of phosphine oxide free radical initiators with a functional wavelength range of about 380 nm to about 450 nm include acyl and bisacyl phosphine oxides such as those described in U.S. Pat. Nos. 4,298,738, 4,324,744 and 4,385,109 and EP 0 173 567. Specific examples of the acylphosphine oxides include 2,4,6-trimethylbenzoyldiphenylphosphine oxide, bis(2,4,6-trimethylbenzoyl)phenylphosphine oxide, dibenzoylphenylphosphine oxide, bis(2,6-dimethoxybenzoyl)phenylphosphine oxide, tris(2,4-dimethylbenzoyl)phosphine oxide, tris(2-methoxybenzoyl)phosphine oxide, 2,6-dimethoxybenzoyldiphenylphosphine oxide, 2,6-dichlorobenzoyldiphenylphosphine oxide, 2,3,5,6-tetramethylbenzoyldiphenylphosphine oxide, benzoyl-bis(2,6-dimethylphenyl) phosphonate, and 2,4,6-trimethylbenzoylethoxyphenylphosphine oxide. Commercially available phosphine oxide photoinitiators capable of free-radical initiation when irradiated at wavelength ranges of greater than about 380 nm to about 450 nm include bis(2,4,6-trimethylbenzoyl)phenyl phosphine oxide (IRGACURE 819), bis(2,6-dimethoxybenzoyl)-(2,4,4-trimethylpentyl) phosphine oxide (CGI 403), a 25:75 mixture, by weight, of bis(2,6-dimethoxybenzoyl)-2,4,4-trimethylpentyl phosphine oxide and 2-hydroxy-2-methyl-1-phenylpropan-1-one (IRGACURE 1700), a 1:1 mixture, by weight, of bis(2,4,6-trimethylbenzoyl)phenyl phosphine oxide and 2-hydroxy-2-methyl-1-phenylpropane-1-one (DAROCUR 4265), and ethyl 2,4,6-trimethylbenzylphenyl phosphinate (LUCIRIN LR8893X). Typically, the phosphine oxide initiator is present in the composition in catalytically effective amounts, such as from 0.1 percent by weight to 5.0 percent by weight, based on the total weight of the composition.

Tertiary amine reducing agents may be used in combination with an acylphosphine oxide Examples of suitable aromatic tertiary amine include N,N-dimethylaniline, N,N-dimethyl-p-toluidine, N,N-dimethyl-m-toluidine, N,N-diethyl-p-toluidine, N,N-dimethyl-3,5-dimethylaniline, N,N-dimethyl-3,4-dimethylaniline, N,N-dimethyl-4-ethylaniline, N,N-dimethyl-4-isopropylaniline, N,N-dimethyl-4-t-butylaniline, N,N-dimethyl-3,5-di-t-butylaniline, N,N-bis(2-hydroxyethyl)-3,5-dimethylaniline, N,N-bis(2-hydroxyethyl)-p-toluidine, N,N-bis(2-hydroxyethyl)-3,4-dimethylaniline, N,N-bis(2-hydroxyethyl)-4-ethylaniline, N,N-bis(2-hydroxyethyl)-4-isopropylaniline, N,N-bis(2-hydroxyethyl)-4-t-butylaniline, N,N-bis(2-hydroxyethyl)-3,5-di-isopropylaniline, N,N-bis(2-hydroxyethyl)-3,5-di-t-butylaniline, 4-N,N-dimethylaminobenzoic acid ethyl ester, 4-N,N-dimethylaminobenzoic acid methyl ester, 4-N,N-dimethylaminobenzoic acid n-butoxyethyl ester, 4-N,N-dimethylaminobenzoic acid 2-(methacryloyloxy) ethyl ester, 4-N,N-dimethylaminobenzophenone ethyl 4-(N,N-dimethylamino) benzoate and N,N-dimethylaminoethyl methacrylate. Examples of an aliphatic tertiary amine include trimethylamine, triethylamine, N-methyldiethanolamine, N-ethyldiethanolamine, N-n-butyldiethanolamine, N-lauryldiethanolamine, triethanolamine, 2-(dimethylamino) ethyl methacrylate, N-methyldiethanolamine dimethacrylate, N-ethyldiethanolamine dimethacrylate, triethanolamine monomethacrylate, triethanolamine dimethacrylate, and triethanolamine trimethacrylate.

The amine reducing agent may be present in the composition in an amount from 0.1 percent by weight to 5.0 percent by weight, based on the total weight of the composition.

Apart from the above mentioned photoinitiators, photoinitiators may be applied having the following formula (XV):

$$X^P\text{-}R^P \qquad (XV)$$

wherein
$X^P$ is a group of the following formula (XVI):

wherein
M is Si or Ge;
$R^6$ represents a substituted or unsubstituted hydrocarbyl or hydrocarbylcarbonyl group;
$R^7$ represents a substituted or unsubstituted hydrocarbyl or hydrocarbylcarbonyl group;
$R^8$ represents a substituted or unsubstituted hydrocarbyl group; and $R^P$ (i) has the same meaning as $X^P$, whereby the compound of formula (XV) may be symmetrical or unsymmetrical; or (ii) is a group of the following formula (XVII):

(XVII)

wherein $Y^P$ represents a single bond, an oxygen atom or a group NR', wherein R' represents a substituted or unsubstituted hydrocarbyl group;

$R^9$ represents a substituted or unsubstituted hydrocarbyl group, a trihydrocarbylsilyl group, a mono(hydrocarbylcarbonyl)dihydrocarbylsilyl group or a di(hydrocarbylcarbonyl)monohydrocarbylsilyl group; or (iii) when M is Si, $R^P$ may be a substituted or unsubstituted hydrocarbyl group.

It was surprisingly found that photoinitiator compounds of formula (XV) represent polymerization initiators which are particularly suitable for dental compositions. With compounds of formula (XV), a high polymerization efficiency is attained, and no coloration problems occur, or in a polymerization system comprising a conventional photoinitiator such as camphor quinone, coloration is efficiently suppressed. Furthermore, compounds of formula (XV) have a light absorption within the wavelength range typically applied in dental application, they are compatible with the ingredients of dental compositions and besides, they are considered physiologically harmless.

Therefore, compounds of formula (XV) are particularly preferred as photoinitiators.

In connection with compound of formula (XV), the term "substituted" as used herein means that $R^6$, $R^7$, $R^8$, $R^9$ and R' may be substituted by a substituent selected from the group consisting of halogen atoms, a nitro group, a cyano group, a hydroxy group, an amino group, $C_{1-6}$ alkyl groups, $C_{1-6}$ alkoxy groups and a —$NR^xR^y$ group wherein $R^x$ and $R^y$ independently from each other represent a $C_{1-6}$ alkyl group. Here, illustrative of the halogen atoms can be fluorine, chlorine, bromine and iodine. The $C_{1-6}$ alkyl groups are, for example, methyl, ethyl, n-propyl, isopropyl and n-butyl. Illustrative of the $C_{1-6}$ alkoxy groups are, for example, methoxy, ethoxy and propoxy. The alkyl moieties in these substituents may be linear, branched or cyclic. Preferably, the substituent is selected from a chlorine atom, a nitro group, a $C_{1-4}$ alkoxy group and a —$NR^xR^y$ group wherein $R^x$ and $R^y$ independently from each other represent a $C_{1-4}$ alkyl group.

If $R^6$, $R^7$ and $R^8$ are substituted, then it is preferred that they are substituted with 1 to 3 substituents, more preferably with 1 substituent.

In the compound of formula (XV), moieties $R^6$, $R^7$ and $R^8$ may be defined as follows:

$R^6$ and $R^7$ independently from each other represent a substituted or unsubstituted hydrocarbyl or hydrocarbylcarbonyl group, and $R^6$ represents a substituted or unsubstituted hydrocarbyl group.

The hydrocarbyl group may be an alkyl group, a cycloalkyl group, a cycloalkylalkyl group, an arylalkyl group or an aryl group.

An alkyl group may be straight-chain or branched $C_{1-20}$ alkyl group, typically a $C_{1-8}$ alkyl group. Examples for a $C_{1-6}$ alkyl group can include linear or branched alkyl groups having 1 to 6 carbon atoms, preferably 1 to 4 carbon atoms, for example, methyl, ethyl, n-propyl, isopropyl, n-butyl, isobutyl, sec-butyl, tert-butyl, n-pentyl, isopentyl and n-hexyl.

A cycloalkyl group may be a $C_{3-20}$ cycloalkyl group, typically a $C_{3-8}$ cycloalkyl group. Examples of the cycloalkyl group can include those having 3 to 6 carbon atoms, for example, cyclopropyl, cyclobutyl, cyclopentyl and cyclohexyl.

A cycloalkylalkyl group may have 4 to 20 carbon atoms and may include a combination of a linear or branched alkyl group having 1 to 6 carbon atoms and a cycloalkyl group having 3 to 14 carbon atoms. Examples of the cycloalkylalkyl(–) group can for example, include methylcyclopropyl(–) methylcyclobutyl(–), methylcyclopentyl(–), methylcyclohexyl(–), ethylcyclopropyl(–), ethylcyclobutyl(–), ethylcyclopentyl(–), ethylcyclohexyl(–), propylcyclopropyl(–), propylcyclobutyl(–), propylcyclopentyl(–), propylcyclohexyl(–).

An arylalkyl(–) group may be a $C_{7-20}$ arylalkyl(–) group, typically a combination of a linear or branched alkyl group having 1 to 6 carbon atoms and an aryl(–) group having 6 to 10 carbon atoms. Specific examples of an arylalkyl(–) group are a benzyl(–) group or a phenylethyl(–) group.

An aryl group can include aryl groups having 6 to 10 carbon atoms. Examples of the aryl group are phenyl and naphtyl.

The hydrocarbylcarbonyl groups of $R^6$ and $R^7$ represent acyl groups ($R_{org}$—(C=O)—) in which the organic residue $R_{org}$ is a hydrocarbyl residue as defined above.

Compound of formula (XV) may contain one or two hydrocarbylcarbonyl groups, that is either one of $R^6$ or $R^7$ is a hydrocarbylcarbonyl group, or both $R^6$ and $R^7$ are hydrocarbylcarbonyl groups. Preferably, compound of formula (XV) contains one hydrocarbylcarbonyl group.

Preferably, the hydrocarbylcarbonyl group is an arylcarbonyl group, more preferably a benzoyl group.

Preferably, $R^6$ and $R^7$ are independently selected from the group consisting of a straight chain or branched $C_{1-6}$ alkyl group, and a phenyl or benzoyl group which may optionally be substituted by one to three substitutents selected from halogen atoms, a nitro group, a $C_{1-4}$ alkoxy group and a —$NR^xR^y$ group wherein $R^x$ and $R^y$ independently from each other represent a $C_{1-4}$ alkyl group, and $R^3$ is a straight chain or branched $C_{1-6}$ alkyl group or a phenyl group.

Most preferably, $R^6$ and $R^7$ are independently selected from the group consisting of a straight chain or branched $C_{1-4}$ alkyl group, and a phenyl or benzoyl group which may optionally be substituted with one substituent selected from the group consisting of selected from a halogen atom, a nitro group, a $C_{1-4}$ alkoxy group and a —$NR^xR^y$ group wherein Rx and $R^y$ independently from each other represent a $C_{1-4}$ alkyl group, and $R^3$ is a straight chain or branched $C_{1-4}$ alkyl group.

In the compound of formula (XV), $R^P$ may have the same meaning as X, whereby the compound of formula (XV) may be symmetrical or unsymmetrical. Alternatively, $R^P$ may represent a substituted or unsubstituted hydrocarbyl group, or a group of formula (XVII). Preferably, if $R^P$ has the same meaning as X, then compound of formula (XV) is unsymmetrical. If $R^P$ represents a substituted or unsubstituted hydrocarbyl group, then the hydrocarbyl group has the same meaning as defined above for $R^6$ and is independently selected therefrom.

In the group of formula (XVII) of compound of formula (XV), $R^9$ represents a substituted or unsubstituted hydrocarbyl group, a trihydrocarbylsilyl group, a mono(hydrocarbylcarbonyl)dihydrocarbylsilyl group or a di(hydrocarbylcarbonyl)monohydrocarbylsilyl group.

If $R^9$ of formula (XVII) is a trihydrocarbylsilyl group, a mono(hydrocarbylcarbonyl)dihydrocarbylsilyl group or a di(hydrocarbylcarbonyl)monohydrocarbylsilyl group, each of the hydrocarbyl and hydrocarbylcarbonyl groups has the same meaning as defined for $R^6$, $R^7$ and $R^8$ and is independently selected therefrom.

In formula (XVII), R' has the same meaning as defined for $R^8$ and is independently selected therefrom.

If M is Si in compound of formula (XV), $R^P$ may be also be a substituted or unsubstituted hydrocarbyl group, wherein the hydrocarbyl group has the same meaning as defined above for $R^8$ and is independently selected therefrom.

For example, compounds of formula (XV) wherein $R^P$ has the same meaning as $X^P$ and which are symmetrical may be have the following structural formulae:

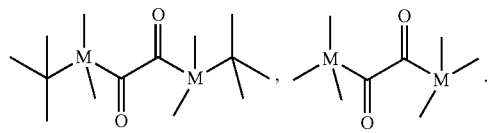

For example, compounds of formula (XV) wherein $R^P$ represents a group of formula (XVII) wherein $Y^P$ is a bond, an oxygen atom or a NR' group, and $R^9$ represents a substituted or unsubstituted hydrocarbyl group may have the following structural formulae:

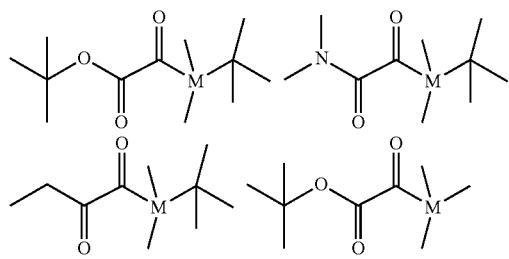

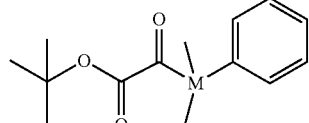

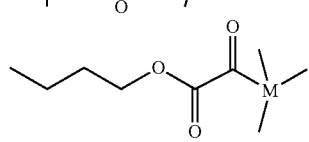

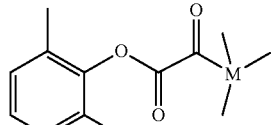

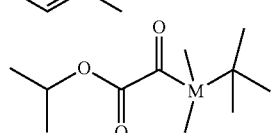

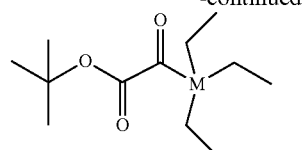

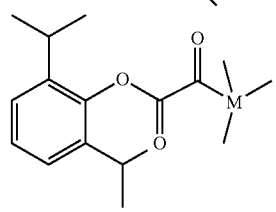

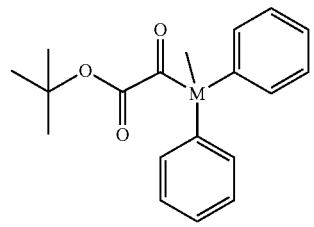

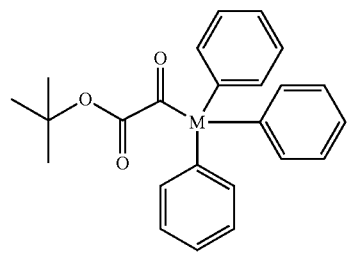

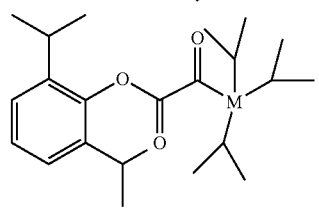

For example, compounds of formula (XV) wherein $R^P$ represents a group of formula (XVII) wherein $R^9$ represents a trihydrocarbylsilyl group have the following structural formulae:

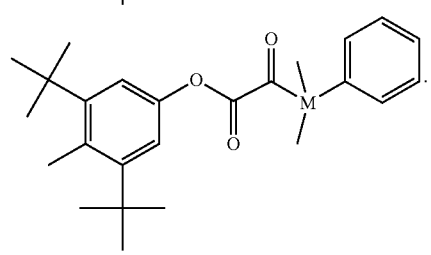

For example, compounds of formula (XV) wherein M is Si and $R^P$ represents a substituted or unsubstituted hydrocarbyl group, may have the following structural formulae:

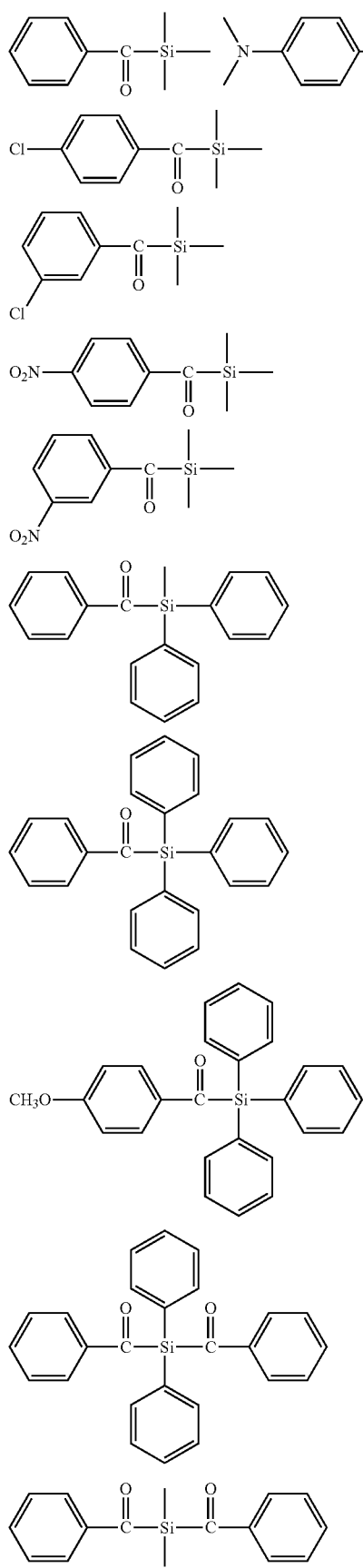
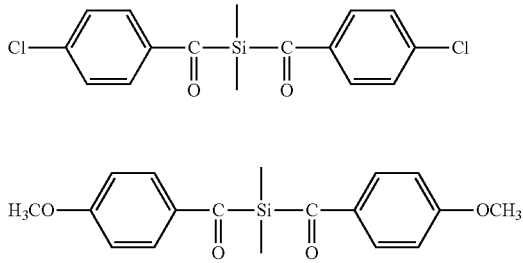
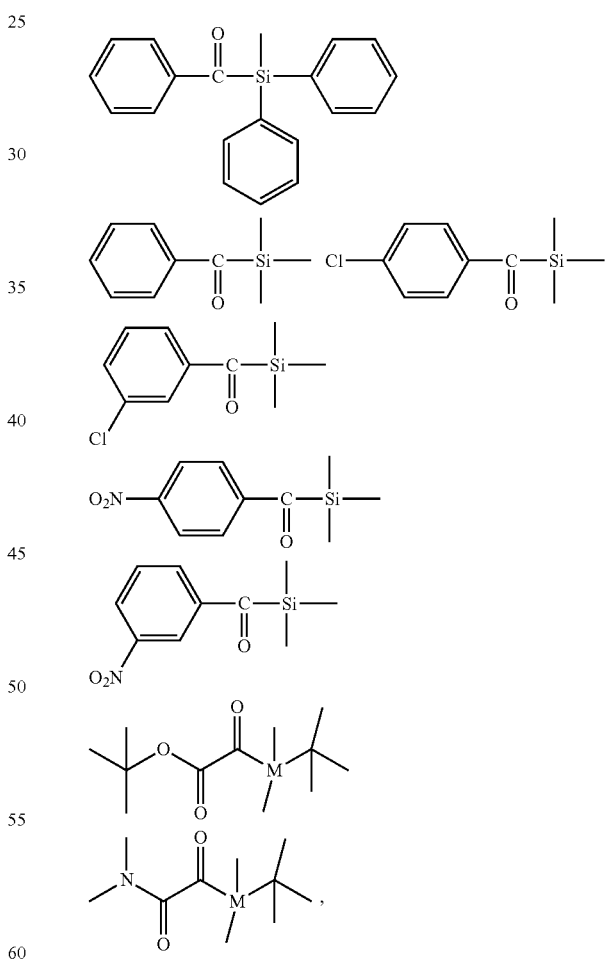
Preferably, compound of formula (XV) is selected from the group consisting of:
wherein compounds of formula (XV) with M=Si are particularly preferred.
Most preferably, compound of formula (XV) is selected from the group consisting of: compound of formula (XV) is selected from the group consisting of:

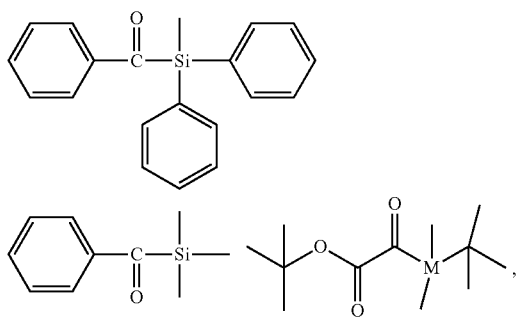

wherein it is particularly preferred that M=Si.

In case the dental composition is in the form of an acidic composition, that is a composition having a pH of less than 7, depending on the composition's pH level, it is preferred to select compounds of formula (XV) with the proviso that they do not contain ester groups, or at least only ester groups which do not significantly hydrolyze in aqueous media at pH 3 at room temperature within one month. Thereby, an advantageous stability of an acidic dental composition, that is a composition having a pH of less than 7, in terms of shelf-life stability of the uncured dental composition as well as stability after curing in the mouth of a patient is ensured. Therefore, for acidic dental compositions, particularly preferred are compounds of formula (XV) excluding $R^P$ being a group of formula (XVII) in which $Y^P$ is an oxygen atom.

Furthermore, since the acylsilyl moiety (—C(=O)—Si—) might be sensitive to basic conditions, that is a pH higher than 7, it is preferred to suitably select a pH value of the composition being higher than 7 with the proviso that the acylsilyl moiety is not cleaved in aqueous media at the selected basic pH at room temperature within one month.

The compound of the formula (XV) may be a known compound which is commercially available or a may be prepared according to published procedures.

The compound of formula (XV) wherein M is Si and $R^P$ represents a substituted or unsubstituted hydrocarbyl group may for example be readily prepared by means of a one-step Pd-catalyzed reaction with a disilane as described e.g. by Yamamoto K. et al., *J. Tetrahedron Lett.*, 1980, vol. 21, pages 1653 to 1656:

Scheme 4 Preparation of acylsilanes

In Scheme 4, the reaction is exemplary depicted with hexamethylsilan as the disilane, whereby a compound of formula (XV) wherein $R^6$, $R^7$ and $R^8$ represent a methyl group is obtained. It is understood that $R^6$, $R^7$ and $R^8$ can be varied by applying disilanes having hydrocarbon substituents other than methyl.

The compound of formula (XV) wherein $R^P$ represents a group of formula (XVII) in which $Y^P$ is an oxygen atom and $R^9$ represents a hydrocarbyl group may for example be prepared by a three-step synthesis as described by Nicewicz D. A. et al. in *Org. Synth.*, 2008, 85, pages 278 to 286. In this three-step synthesis, an acetoacetate is converted to an azide compound, which is then reacted with a trihydrocarbylsilyl-trifluoromethane-sulfonate to obtain a trihydrocarbylsilyldiazoacetate, which is finally reacted with potassium peroxymonosulfate to arrive at the target compound:

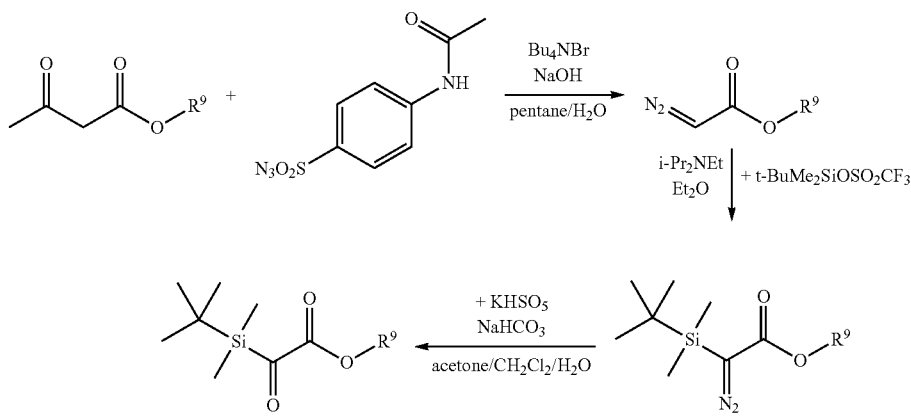

Scheme 5 Preparation of silylglyoxylates

In Scheme 5, the reaction is exemplary depicted for obtaining a compound of formula (XV) wherein $R^9$ of group (XVII) represents a hydrocarbyl group in the form of tert-butyl. It is understood that $R^9$ can be varied by applying an acetoacetate other than tert-butyl acetoacetate.

Alternatively, compounds of formula (XV) wherein M is Si, $R^P$ represents a group of formula (XVII) and $Y^P$ represents an oxygen atom may be prepared by a single-pot three-component coupling reaction of a silylglyoxylate, a terminal alkyne and an aldehyde in the presence of $ZnI_2$ and $Et_3N$ as described by Nicewicz D. A. in J. Am. Chem. Soc., 2005, 127 (17), pages 6170 to 6171. Further syntheses of silylglyoxylate compounds are described e.g. by Boyce G. R. et al. in *J. Org. Chem.*, 2012, 77 (10), pages 4503 to 4515 and Boyce G. R. et al. in Org. Lett., 2012, 14 (2), pages 652 to 655.

For example, the following compounds of formula (XV) are known and commercially available, and their Chemical Abstracts (CAS) No. is given in brackets: benzoyltriphenylsilane (1171-49-9), benzoyltrimethylsilan (5908-41-8), 1-[(trimethylsilyl) carbonyl]-naphthalene (88313-80-8), 1-methoxy-2-[(trimethylsilyl)-carbonyl]-benzene (107325-71-3), (4-chlorobenzoyl) (triphenyl) silane (1172-90-3), (4-nitrobenzoyl) (triphenyl) silane (1176-24-5), (methyldiphenylsilyl)phenyl-methanone (18666-54-1), (4-methoxybenzoyl) triphenylsilan (1174-56-7) and tert-butyl (tert-butyldimethylsilyl)glyoxylate (852447-17-7).

All compounds of formula (XV) comprise the group of formula (XVI)

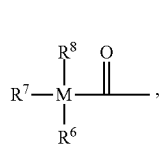

(XVI)

wherein M, $R^6$, $R^7$ and $R^8$ are defined as above. Depending on the selection of M, the group of formula (XVI) represents an acylsilane or acylgermane group. Upon exposure to UV-VIS-light, the bond between M and the acyl group may be cleaved, whereby a silyl/germanyl and an acyl radical is formed as a polymerization initiating structure, but in competition to the cleavage into to radicals, a carbene structure might be formed:

Scheme 6 carbene formation versus radical formation

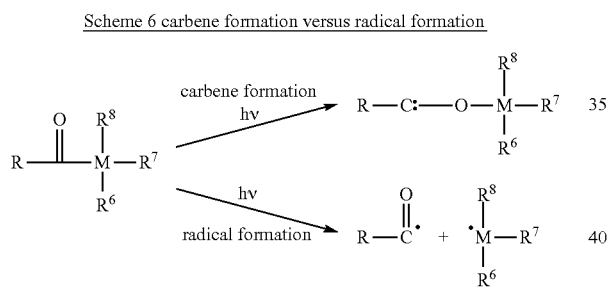

This competition between the formation of polymerization initiating radicals and carbene formation is described for acylsilanes by El-Roz, M. et al. in Current Trends in Polymer Science, 2011, vol. 15, pages 1 to 13.

Besides, in case in compound of formula (XV) wherein $R^P$ has the same meaning as $X^P$ or is a group of formula (XVII), the C—C bond of the 1,2-diketone moiety (—C(=O)—C(=O)—) may be cleaved upon exposure to UV-VIS-light into two acyl radicals. This cleavage is exemplary shown for compound of formula (XV) wherein $R^P$ is a group of formula (XVII) and $Y^P$ is an oxygen atom, that is for a glyoxylate (—O—C=O)—C(=O)—) compound:

Scheme 7 cleavage of
—O—C(=O)—C(=O)—
moiety of a glyoxylate

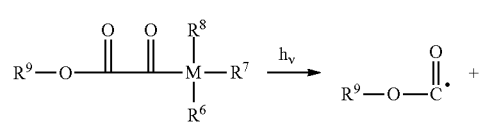

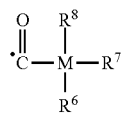

Besides, in compound of formula (XV), there is a third possibility for a radical cleavage in case $R^P$ is a compound of formula (XVII) wherein $Y^P$ is an oxygen atom and $R^9$ is a substituted or unsubstituted hydrocarbyl group. Namely, an intra- or intermolecular hydrogen abstraction might occur, where a hydrogen radical is abstracted:

Scheme 8 hydrogen abstraction (intra- or intermolecular)

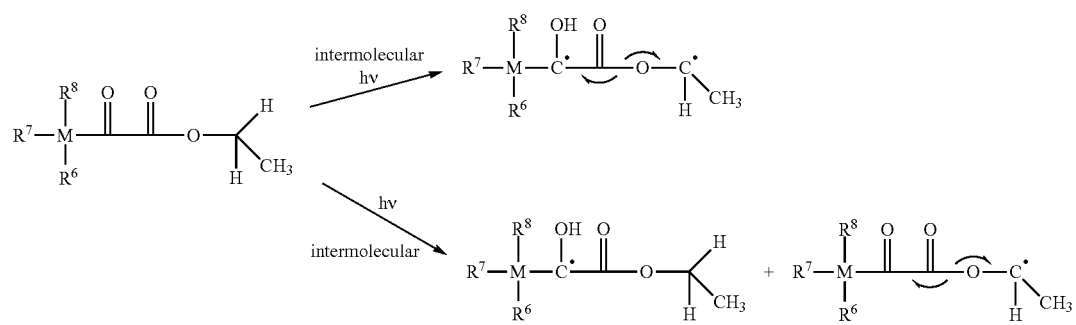

Both the cleavage of a glyoxylate group and the hydrogen abstraction mechanism is known for photoinitiators which do not contain silicium or germanium, such as ethyl phenylglyoxylate (Irgacure® MBF).

For compounds of formula (XV) wherein $R^P$ has the same meaning as $X^P$ or is a group of formula (XVII), the present inventors carried out molecular modelling calculations from which it appears that a Si—C or Ge—C bond cleavage can be ruled out, since the C—C bond of the —C(=O)—C(=O)— moiety is weaker than the Si—C or Ge—C bond.

The photoinitiator system may further comprise diaryl iodonium salts, triaryl sulfonium salts and tetraaryl or tetraalkyl phosphonium salts. These salts may serve as a coinitiator for improving the polymerization performance of the photoinitiator, but they may also serve as an initiator for cationic polymerization.

For example, diaryl iodonium salt may be selected from the group consisting of (4-methylphenyl)[4-(2-methylpropyl) phenyl] iodonium hexafluoroantimonate, include (4-methylphenyl)[4-(2-methylpropyl) phenyl] iodonium tetrafluoroborate, diphenyliodonium (DPI) tetrafluoroborate, di(4-methylphenyl)iodonium (Me2-DPI) tetrafluoroborate, phenyl-4-methylphenyliodonium tetrafluoroborate, di(4-heptylphenyl)iodonium tetrafluoroborate, di(3-nitrophenyl) iodonium hexafluorophosphate, di(4-chlorophenyl)iodonium hexafluorophosphate, di(naphthyl)iodonium tetrafluoroborate, di(4-trifluoromethylphenyl)iodonium tetrafluoroborate, DPI hexafluorophosphate, Me2-DPI hexafluorophosphate; DPI hexafluoroarsenate, di(4-phenoxyphenyl)iodonium tetrafluoroborat, phenyl-2-thienyliodonium hexafluorophosphate, 3,5-dimethylpyrazolyl-4-phenyliodonium hexafluorophosphate, DPI hexafluoroantimonate, 2,2'-DPI tetrafluoroborate, di(2,4-dichlorophenyl)iodonium hexafluorophosphate, di(4-bromophenyl)iodonium hexafluorophosphate, di(4-methoxyphenyl)iodonium hexafluorophosphate, di(3-carboxyphenyl)iodonium hexafluorophosphate, di(3-methoxycarbonylphenyl)iodonium hexafluorophosphate, di(3-methoxysulfonylphenyl)iodonium hexafluorophosphate, di(4-acetamidophenyl)iodonium hexafluorophosphate, di(2-benzothienyl)iodonium hexafluorophosphate, and DPI hexafluorophosphate.

Particularly preferred iodonium compounds include diphenyliodonium (DPI) hexafluorophosphate, di(4-methylphenyl)iodonium (Me2-DPI) hexafluorophosphate, diaryliodonium hexafluoroantimonate, (4-methylphenyl)[4-(2-methylpropyl) phenyl] iodonium hexafluoroantimonate, (4-methylphenyl)[4-(2-methylpropyl)phenyl]iodonium hexafluorophosphate (Irgacure® 250, commercial product available from BASF SE), (4-methylphenyl)[4-(2-methylpropyl) phenyl] iodonium tetrafluoroborate, 4-octyloxyphenyl phenyliodonium hexafluoroantimonate, 4-(2-hydroxytetradecyloxyphenyl)phenyliodonium hexafluoroantimonate, and 4-isopropyl-4'-methyldiphenyliodonium borate.

According to a particularly preferred embodiment, the iodonium compound is DPI hexafluorophosphate and/or 4-isopropyl-4'-methyldiphenyliodonium tetrakis(pentafluorophenyl) borate.

A preferred triaryl sulfonium salt is S-(phenyl)thianthrenium hexafluorophosphate of the following formula:

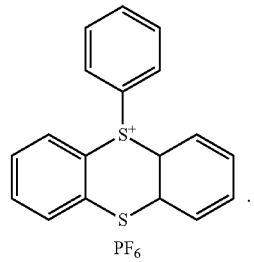

Particularly preferred phosphonium salts are the tetraalkyl phosphonium salts tetrakis-(hydroxymethyl)-phosphonium (THP) salt or a tetrakis-(hydroxymethyl)-phosphonium hydroxide (THPOH) salt, wherein the anion of the tetraalkyl phosphonium salt is selected from the group consisting of formate, acetate, phosphate, sulphate, fluoride, chloride, bromide and iodide.

A particularly preferred photoinitiator system comprises a photoinitiators of formula (XV), optionally in addition with camphor quinone, in combination with a diaryl iodonium salt, triaryl sulfonium salt or a tetraaryl or tetraalkyl phosphonium salt as described above.

A suitable redox initiator system comprises reducing and oxidizing agents, which produce free-radicals capable of initiating polymerization of the polymerizable group(s) of component (i) or further polymerizable compounds independent from the presence of light. The reducing and oxidizing agents are selected so that the initiator system (ii) is sufficiently storage-stable and free of undesirable colorization to permit storage and use under typical dental conditions. Moreover, the reducing and oxidizing agents are selected so that the initiator system (ii) is sufficiently miscible with the resin system to permit dissolution of the initiator system in the composition.

Useful reducing agents include ascorbic acid, ascorbic acid derivatives, and metal complexed ascorbic acid compounds as described in U.S. Pat. No. 5,501,727; amines, namely tertiary amines, such as 4-tert-butyl dimethylaniline; aromatic sulfinic salts, such as p-toluenesulfinic salts and benzenesulfinic salts; thioureas, such as 1-ethyl-2-thiourea, tetraethyl thiourea, tetramethyl thiourea, 1,1-dibutyl thiourea, and 1,3-dibutyl thiourea; and mixtures thereof. Other secondary reducing agents may include cobalt (II) chloride, ferrous chloride, ferrous sulfate, hydrazine, hydroxylamine, salts of a dithionite or sulfite anion, and mixtures thereof.

Suitable oxidizing agents include persulfuric acid and salts thereof, such as ammonium, sodium, potassium, cesium, and alkyl ammonium salts. Additional oxidizing agents include peroxides such as benzoyl peroxides, hydroperoxides such as cumyl hydroperoxide, t-butyl hydroperoxide, and amyl hydroperoxide, as well as salts of transition metals such as cobalt (III) chloride and ferric chloride, cerium (IV) sulfate, perboric acid and salts thereof, permanganic acid and salts thereof, perphosphoric acid and salts thereof, and mixtures thereof. One or more different oxidizing agents or one or more different reducing agent may be used in the initiator system. Small quantities of transition metal compounds may also be added to accelerate the rate of redox cure. The reducing and oxidizing agents are present in amounts sufficient to permit an adequate free-radical reaction rate.

The reducing or oxidizing agents may be microencapsulated for enhancing shelf stability of the composition, and if necessary permitting packaging the reducing and oxidizing agents together (U.S. Pat. No. 5,154,762). Appropriate selection of an encapsulant may allow combination of the oxidizing and reducing agents and even of an acid-functional component and optional filler in a storage-stable state. Moreover, appropriate selection of a water-insoluble encapsulant allows combination of the reducing and oxidizing agents with the particulate reactive glass and water in a storage-stable state.

The amount of active species of the initiator system is not particularly limited. Suitably, the amount of photoinitiator in the initiator system (ii) is in the range of from 0.001 to 5 mol % based on the total amount of the monomers such as component (i) or further polymerizable compounds described below.

Further Polymerizable Compounds

Besides of (i) the acidic polymerizable compound of formula (I), the dental composition of the present invention may further contain one or more polymerizable compounds having at least one polymerizable group, which further compound(s) differ(s) from the acidic polymerizable compound of formula (I).

The polymerizable group of the further contained one or more polymerizable compounds is not particularly limited. The at least one polymerizable group may for example be a radically polymerizable carbon-carbon double bond and/or a cationically polymerizable group.

Preferably, radically polymerizable carbon-carbon double bonds are selected from carbon-carbon double bonds of (meth)acryloyl group(s) and a (meth)acrylamide group, preferably (meth)acryloyl group(s). Further, it is preferred that the cationically polymerizable groups are selected from epoxide groups, oxetane groups, vinyl ether groups, aziridine groups, and azetidine groups, preferably from epoxide groups, vinyl ether groups and oxetane groups, most preferably from epoxide groups and vinyl ether groups.

The optionally further contained compound(s) having at least one radically polymerizable carbon-carbon double bonds are not particularly limited. However, preferably, their radically polymerizable carbon-carbon double bonds are selected from carbon-carbon double bonds of a (meth)acryloyl group and a (meth)acrylamide group.

Suitable examples of compounds having at least one radically polymerizable carbon-carbon double bonds may be selected from the group consisting of (meth)acrylates, amides of acrylic or methacrylic acid, urethane acrylates or methacrylates, and polyol acrylates or methacrylates.

(Meth)acrylates may be preferably selected from compounds of the following formulae (A), (B) and (C):

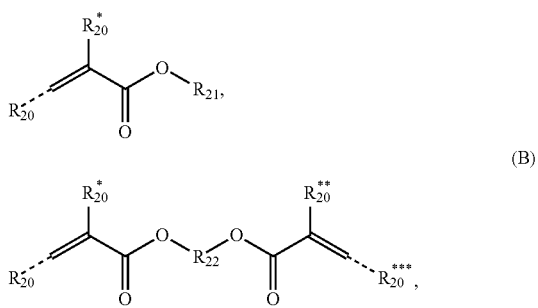

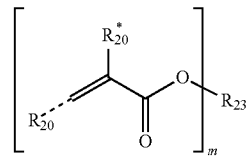

wherein $R_{20}$, $R^*_{20}$, $R^{}_{20}$, $R^{*}_{20}$ independently represent a hydrogen atom, —COOM, a linear $C_{1-18}$ or branched $C_{3-18}$ alkyl group which may be substituted by a $C_{3-6}$ cycloalkyl group, a $C_{6-14}$ aryl or $C_{3-14}$ heteroaryl group, —COOM, —PO$_3$M, —O—PO$_3$M$_2$ or —SO$_3$M*, a $C_3$ to $C_{18}$ cycloalkyl group which may be substituted by a $C_{1-16}$ alkyl group, a $C_{6-14}$ aryl or $C_{3-14}$ heteroaryl group, or a $C_5$ to $C_{18}$ aryl or $C_3$ to $C_{18}$ heteroaryl group, —COOM, —PO$_3$M, —O—PO$_3$M$_2$ or —SO$_3$M*, $R_{21}$ represents a hydrogen atom, a linear $C_{1-18}$ or branched $C_{3-18}$ alkyl group or $C_2$ to $C_{18}$ alkenyl group which may be substituted by a $C_{3-6}$ cycloalkyl group, a $C_{6-14}$ aryl or $C_{3-14}$ heteroaryl group, —COOM, —PO$_3$M, —O—PO$_3$M$_2$ or —SO$_3$M*, a $C_3$ to $C_{18}$ cycloalkyl group which may be substituted by a $C_{1-16}$ alkyl group, a $C_{6-14}$ aryl or $C_{3-14}$ heteroaryl group, —COOM, —PO$_3$M, —O—PO$_3$M$_2$ or —SO$_3$M*, or a $C_5$ to $C_{18}$ aryl or $C_3$ to $C_{18}$ heteroaryl group, $R_{22}$ represents a divalent organic residue having from 1 to 45 carbon atoms, whereby the divalent organic residue may contain at least one of from 1 to 7 $C_{3-12}$ cycloalkylene group(s), 1 to 7 $C_{6-14}$ arylene groups, 1 to 7 carbonyl groups, 1 to 7 carboxyl groups (—(C=O)—O— or —O—(C=O)—), 1 to 7 amide groups (—(C=O)—NH— or —NH—(C=O)—) or 1 to 7 urethane groups (—NH—(C=O)—O— or —O—(C=O)—NH—), and 1 to 14 heteroatoms selected from oxygen, nitrogen and sulphur, which divalent organic residue may be substituted with one or more substituents selected from the group consisting of a hydroxyl group, a thiol group, a $C_{8-14}$ aryl group, —COOM, —PO$_3$M, —O—PO$_3$M$_2$ or —SO$_3$M*; preferably $R_{22}$ is a $C_1$ to $C_{18}$ alkylene group which may be substituted by one or more —OH group(s), which alkylene group may contain at least one of 1 to 4 $C_{8-10}$ arylene groups, 1 to 4 urethane groups (—NH—(C=O)—O— or —O—(C=O)—NH—), and 1 to 8 oxygen atoms;

$R_{23}$ represents a saturated di- or multivalent substituted or unsubstituted $C_2$ to $C_{18}$ hydrocarbon group, a saturated di- or multivalent substituted or unsubstituted cyclic $C_3$ to $C_{18}$ hydrocarbon group, a di- or multivalent substituted or unsubstituted $C_4$ to $C_{18}$ aryl or heteroaryl group, a di- or multivalent substituted or unsubstituted $C_5$ to $C_{18}$ alkylaryl or alkylheteroaryl group, a di- or multivalent substituted or unsubstituted $C_7$ to $C_{30}$ aralkyl group, or a di- or multivalent substituted or unsubstituted $C_2$ to $C_{45}$ mono-, di-, or polyether residue having from 1 to 14 oxygen atoms, and m is an integer, preferably in the range from 1 to 10, wherein M of any one of $R_{20}$, $R^*_{20}$, $R^{}_{20}$, $R^{*}_{20}$, $R_{21}$, and $R_{22}$, which M are independent from each other, each represent a hydrogen atom or a metal atom, and M* of any one of $R_{20}$, $R^*_{20}$, $R^{}_{20}$, $R^{*}_{20}$, $R_{21}$, and $R_{22}$, which M are independent from each other, each represent a metal atom.

For $R_{20}$, $R^*_{20}$, $R^{}_{20}$ and $R^{*}_{20}$, the linear $C_{1-18}$ or branched $C_{3-18}$ alkyl group may e.g. be methyl, ethyl, n-propyl, i-propyl, n-butyl, isobutyl, tert-butyl, sec-butyl, pentyl or hexyl. For $R_{21}$ and $R^*_{21}$, the $C_{1-18}$ alkyl group or $C_{2-18}$ alkenyl group may e.g. be eth(en)yl, n-prop(en)yl, i-prop(en)yl, n-but(en)yl, isobut(en)yl, tert-but(en)yl sec-but(en)yl, pent(en)yl or hex(en)yl.

For $R_{20}$, $R^*_{20}$, $R^{}_{20}$, $R^{*}_{20}$ and $R_{21}$ an aryl group may, for example, be a phenyl group or a naphthyl group, and a $C_{3-14}$ heteroaryl group may contain 1 to 3 heteroatoms selected from nitrogen, oxygen and sulfur.

For $R_{22}$, in the phrase "divalent organic residue may contain at least one of . . . " means that the groups which may be contained in the divalent organic residue are incorporated in the divalent organic residue by means of covalent bonding. For example, in BisGMA, two aryl groups in the form of phenyl and two heteroatoms in the form of oxygen are incorporated into the divalent organic residue of $R_{22}$. Or, as a further example, in UDMA, two urethane groups (—NH—(C=O)—O— or —O—(C=O)—NH—) are incorporated in the divalent organic residue of $R_{22}$.

In formula (B), the dotted bond indicates that $R_{20}$ and $R^{***}_{20}$ may be in (Z) or (E) configuration relative to CO.

Preferably, in formulae (A), (B) and (C), $R_{20}$, $R^*_{20}$, $R^{}_{20}$ and $R^{*}_{20}$ independently represent a hydrogen atom, a linear $C_{1-16}$ or branched $C_{3-16}$ alkyl group which may be substituted by a $C_{3-6}$ cycloalkyl group, a $C_{6-14}$ aryl or $C_{3-14}$ heteroaryl group, a $C_{3-6}$ cycloalkyl group which may be substituted by a $C_{1-16}$ alkyl group, a $C_{6-14}$ aryl or $C_{3-14}$ heteroaryl group, a $C_{6-14}$ aryl or $C_{3-14}$ heteroaryl group. More preferably, in formula (B), $R_{20}$, $R^*_{20}$, $R^{}_{20}$ and $R^{*}_{20}$ independently represent a hydrogen atom, a linear $C_{1-8}$ or branched $C_{3-8}$ alkyl group which may be substituted by a $C_{4-6}$ cycloalkyl group, a $C_{6-10}$ aryl or $C_{4-10}$ heteroaryl group, a $C_{4-6}$ cycloalkyl group which may be substituted by a $C_{1-6}$ alkyl group, a $C_{6-10}$ aryl or $C_{4-10}$ heteroaryl group or a $C_{6-10}$ aryl group. Even more preferably, $R_{20}$, $R^*_{20}$, $R^{}_{20}$ and $R^{*}_{20}$ independently represent a hydrogen atom, a linear $C_{1-4}$ or branched $C_3$ or $C_4$ alkyl group which may be substituted by a cyclohexyl group or a phenyl group, or a cyclohexyl group which may be substituted by a $C_{1-4}$ alkyl group. Most preferably, $R_{20}$, $R^*_{20}$, $R^{}_{20}$ and $R^{*}_{20}$ independently represent a hydrogen atom or a linear $C_{1-4}$ or branched $C_3$ or $C_4$ alkyl group.

Preferably, in formula (A), $R_{21}$ represents a hydrogen atom, a linear $C_{1-16}$ or branched $C_{3-16}$ alkyl group or $C_{2-16}$ alkenyl group which may be substituted by a $C_{3-6}$ cycloalkyl group, a $C_{6-14}$ aryl or $C_{3-14}$ heteroaryl group, a $C_{3-6}$ cycloalkyl group which may be substituted by a $C_{1-16}$ alkyl group, a $C_{6-14}$ aryl or $C_{3-14}$ heteroaryl group, a $C_{6-14}$ aryl or $C_{3-14}$ heteroaryl group. More preferably, $R_{21}$ represents a hydrogen atom, a linear $C_{1-10}$ or branched $C_{3-10}$ alkyl or $C_{2-10}$ alkenyl group group which may be substituted by a $C_{4-6}$ cycloalkyl group, a $C_{6-10}$ aryl or $C_{4-10}$ heteroaryl group, a $C_{4-6}$ cycloalkyl group which may be substituted by a $C_{1-6}$ alkyl group, a $C_{6-10}$ aryl or $C_{4-10}$ heteroaryl group or a $C_{6-10}$ aryl group. Even more preferably, $R_{21}$ represents is a hydrogen atom, a linear $C_{1-10}$ or branched $C_{3-10}$ alkyl group or linear $C_{2-10}$ or branched $C_{3-10}$ alkenyl group which may be substituted by a cyclohexyl group or a phenyl group, or a cyclohexyl group which may be substituted by a $C_{1-4}$ alkyl group. Yet even more preferably, $R_{21}$ represents an unsubstituted $C_{1-10}$ alkyl group or $C_{2-10}$ alkenyl group, still even more preferably an unsubstituted $C_{2-6}$ alkyl group or $C_{3-6}$ alkenyl group, and most preferably an ethyl group or an allyl group.

The (meth)acrylate compounds of formulae (A), (B) and (C) may be selected from the group consisting of methyl acrylate, methyl methacrylate, ethyl acrylate, ethyl methacrylate, propyl acrylate, propyl methacrylate, isopropyl acrylate, isopropyl methacrylate, 2-hydroxyethyl acrylate, 2-hydroxyethyl methacrylate (HEMA), hydroxypropyl acrylate, hydroxypropyl methacrylate, tetrahydrofurfuryl acrylate, tetrahydrofurfuryl methacrylate, glycidyl acrylate, glycidyl methacrylate, bisphenol A glycerolate dimethacrylat ("bis-GMA", CAS-No. 1565-94-2), 4,4,6,16 (or 4,6,6,16)-tetramethyl-10,15-dioxo-11,14-dioxa-2,9-diazaheptadec-16-enoicacid 2-[(2-methyl-1-oxo-2-propen-1-yl)oxy]ethyl ester (CAS no. 72869-86-4)_(UDMA), glycerol mono-and di-acrylate such as 1,3-glycerol dimethacrylate (GDM), glycerol mono- and dimethacrylate, ethyleneglycol diacrylate, ethyleneglycol dimethacrylate, polyethyleneglycol diacrylate (where the number of repeating ethylene oxide units vary from 2 to 30), polyethyleneglycol dimethacrylate (where the number of repeating ethylene oxide units vary from 2 to 30 especially triethylene glycol dimethacrylate ("TEGDMA"), neopentyl glycol diacrylate, neopentylglycol dimethacrylate, trimethylolpropane triacrylate, trimethylol propane trimethacrylate, mono-, di-, tri-, and tetra-acrylates and methacrylates of pentaerythritol and dipentaerythritol, 1,3-butanediol diacrylate, 1,3-butanediol dimethacrylate, 1,4-butanedioldiacrylate, 1,4-butanediol dimethacrylate, 1,6-hexane diol diacrylate, 1,6-hexanediol dimethacrylate, di-2-methacryloyloxethyl hexamethylene dicarbamate, di-2-methacryloyloxyethyl trimethylhexanethylene dicarbamate, di-2-methacryloyl oxyethyl dimethylbenzene dicarbamate, methylene-bis-2-methacryloxyethyl-4-cyclohexyl carbamate, di-2-methacryloxyethyl-dimethylcyclohexane dicarbamate, methylene-bis-2-methacryloxyethyl-4-cyclohexyl carbamate, di-1-methyl-2-methacryloxyethyl-trimethylhexamethylene dicarbamate, di-1-methyl-2-methacryloxyethyl-dimethylbenzene dicarbamate, di-1-methyl-2-methacryloxyethyl-dimethylcyclohexane dicarbamate, methylene-bis-1-methyl-2-methacryloxyethyl-4-cyclohexyl carbamate, di-1-chloromethyl-2-methacryloxyethyl-hexamethylene dicarbamate, di-1-chloromethyl-2-methacryloxyethyl-trimethylhexamethylene dicarbamate, di-1-chloromethyl-2-methacryloxyethyl-dimethylbenzene dicarbamate, di-1-chloromethyl-2-methacryloxyethyl-dimethylcyclohexane dicarbamate, methylene-bis-2-methacryloxyethyl-4-cyclohexyl carbamate, di-1-methyl-2-methacryloxyethyl-hexamethylene dicarbamate, di-1-methyl-2-methacryloxyethyl-trimethylhexamethylene dicarbamate, di-1-methyl-2-methacryloxyethyl-dimethylbenzene dicarbamate, di-1-methyl-2-metha-cryloxyethyl-dimethylcyclohexane dicarbamate, methylene-bis-1-methyl-2-methacryloxyethyl-4-cyclohexyl carbamate, di-1-chloromethyl-2-methacryloxyethyl-hexamethylene dicarbamate, di-1-chloromethyl-2-methacryloxyethyl-trimethylhexamethylene dicarbamate, di-1-chloromethyl-2-methacryloxyethyl-dimethylbenzene dicarbamate, di-1-chloromethyl-2-methacryloxyethyl-dimethylcyclohexane dicarbamate, methylene-bis-1-chloromethyl-2-methacryloxyethyl4-cyclohexyl carbamate, 2,2'-bis(4-methacryloxyphenyl)propane, 2,2'bis(4-acryloxyphenyl)propane, 2,2'-bis[4(2-hydroxy-3-methacryloxy-phenyl)]propane, 2,2'-bis[4(2-hydroxy-3-acryloxy-phenyl)propane, 2,2'-bis(4-methacryloxyethoxyphenyl)propane, 2,2'-bis-(4-acryloxyethoxyphenyl)propane, 2,2'-bis(4-methacryloxypropoxyphenyl)propane, 2,2'-bis(4-acryloxypropoxyphenyl)propane, 2,2'-bis(4-methacryloxydiethoxyphenyl)propane, 2,2'-bis(4-acryloxydiethoxyphenyl)propane, 2,2'-bis[3(4-phenoxy)-2-hydroxypropane-1-methacrylate]propane, and 2,2'-bis[3(4-phenoxy)-2-hydroxypropane-1-acrylate]propane.

Most preferably, a compound of formula (B) is selected from the group consisting of:

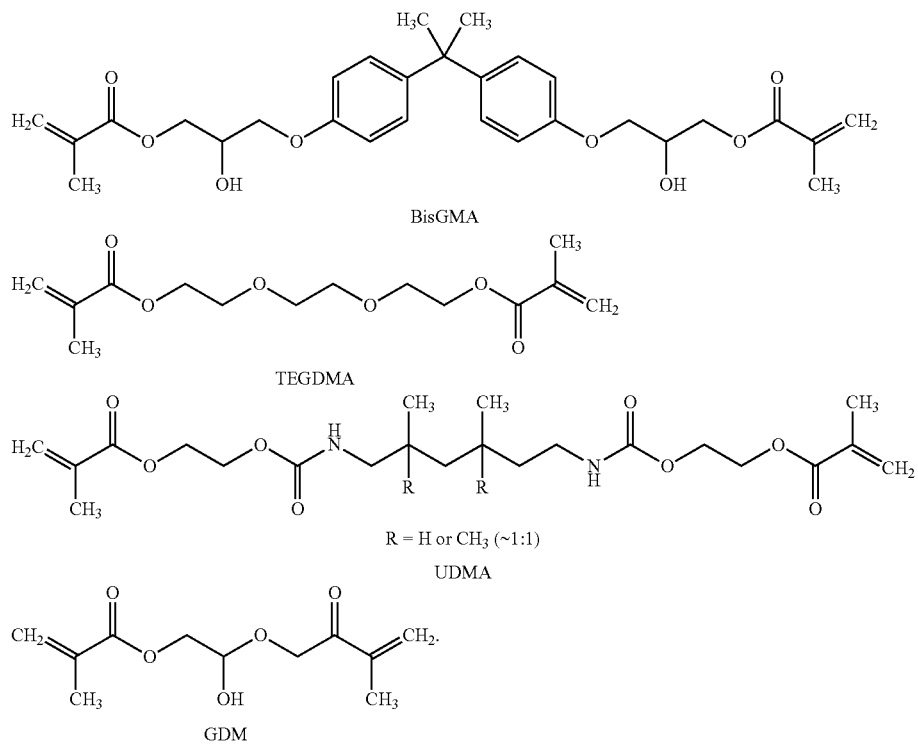

BisGMA

TEGDMA

R = H or CH₃ (~1:1)
UDMA

GDM

Particular preferred mono- or bis- or (meth)acrylamides and poly[(meth) acrylamides] have the following formulae (D), (E) and (F):

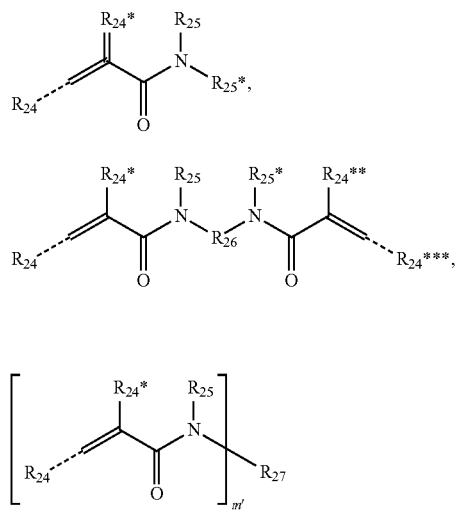

wherein $R_{24}$ $R^*_{24}$, $R^{}_{24}$, $R^{*}_{24}$ have the same meaning as $R_{20}$ $R^*_{20}$, $R^{}_{20}$, $R^{*}_{20}$ defined above for formulae (A), (B) and (C), $R_{25}$, $R^*_{25}$ independently represent a residue having the same meaning as $R_{21}$ defined above for formula (A), and $R_{27}$ and m' have the same meaning as $R_{23}$ and m defined above for formula (C).

In formula (E), $R_{26}$ represents a divalent substituted or unsubstituted organic residue having from 1 to 45 carbon atoms, whereby said organic residue may contain at least one of 1 to 7 $C_{3-12}$ cycloalkylene group(s), 1 to 7 $C_{6-14}$ arylene groups, from 1 to 7 carbonyl groups, 1 to 7 carboxyl groups (—(C=O)—O— or —O—(C=O)—), 1 to 7 amide groups (—(C=O)—NH— or —NH—(C=O)—), 1 to 7 urethane groups (—NH—(C=O)—O— or —O—(C=O)—NH—), and 1 to 14 heteroatoms selected from oxygen, nitrogen and sulphur, which divalent organic residue may be substituted with one or more substituent(s) selected from the group consisting of a hydroxyl group, a thiol group, a $C_{6-14}$ aryl group, —COOM, —PO₃M, —O—PO₃M₂ or —SO₃M*; preferably $R_{26}$ is a $C_1$ to $C_{18}$ alkylene group or a $C_2$ to $C_{18}$ alkenylene group which may contain at least one of 1 to 4 $C_{6-10}$ arylene groups and $C_{3-8}$ cycloalkylene group, 1 to 4 urethane groups (—NH—(C=O)—O— or —O—(C=O)—NH—), and 1 to 8 oxygen atoms or nitrogen atoms.

For $R_{26}$, the phrase "divalent organic residue may contain at least one of . . . " has an analogous meaning as defined above for $R_{22}$ of compound of formula (B).

In formulae (D), (E), (F), the dotted bond indicates that $R_{24}$ and $R^{***}_{24}$ may be in (Z) or (E) configuration relative to CO.

In compound of formula (D), $R_{25}$ and $R_{25}*$ may cooperatively form a ring in which $R_{25}$ and $R_{25}*$ are linked by a C—C bond or a functional group selected from the group consisting of an ether group, a thioether group, an amine group and an amide group.

Preferred methacrylamides according to formulae (D), (E), (F) have the following formulae:
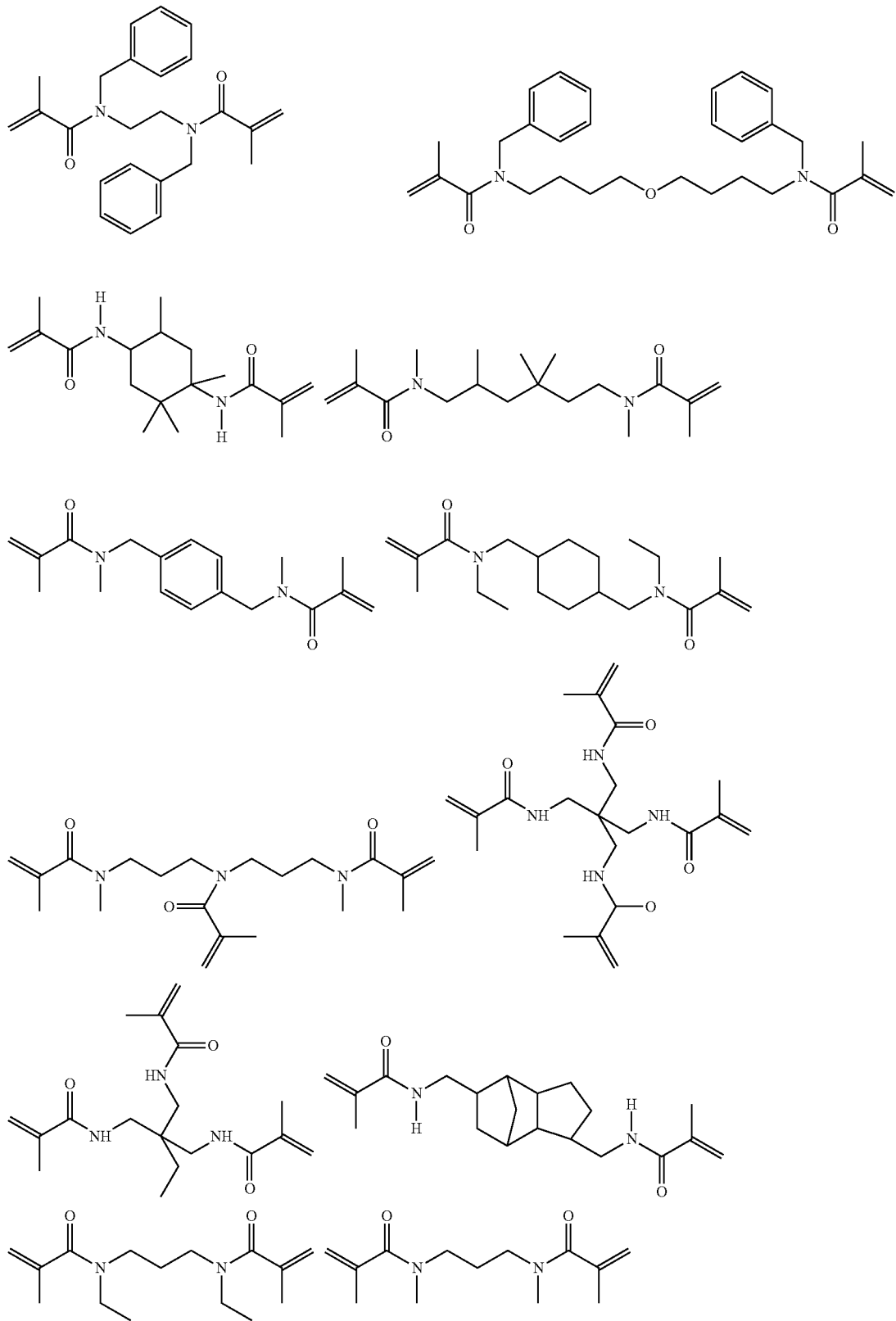

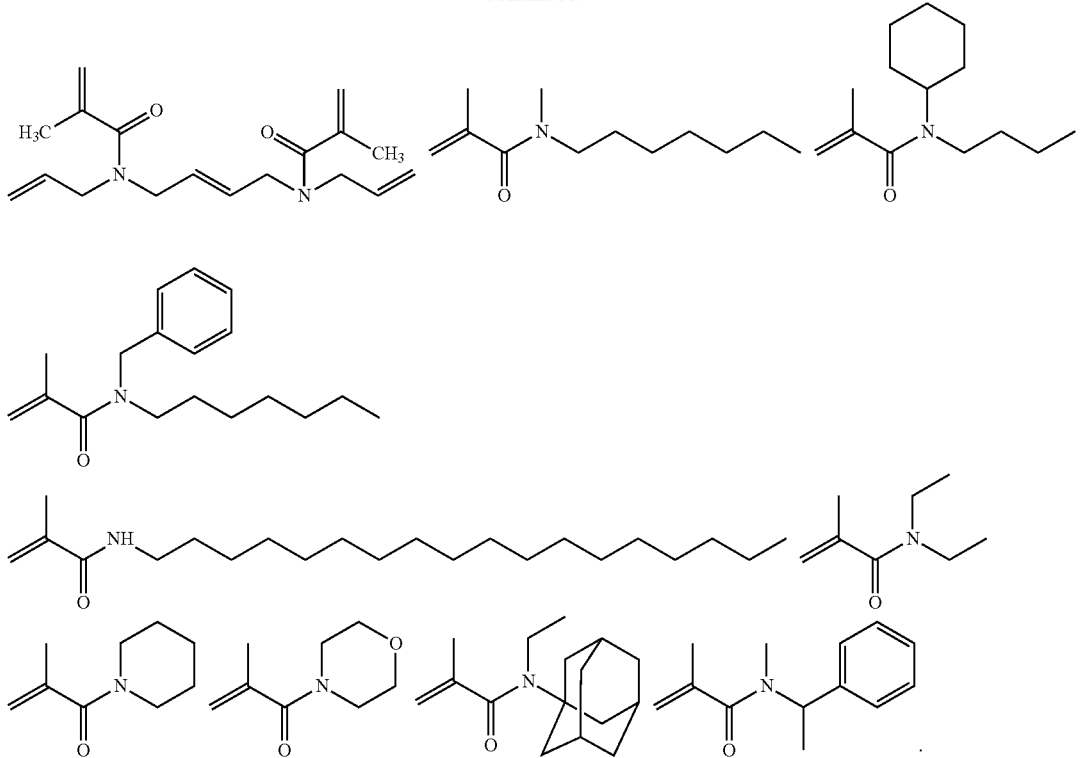
Preferred acrylamides according to formulae (D), (E), (F) have the following formulae:
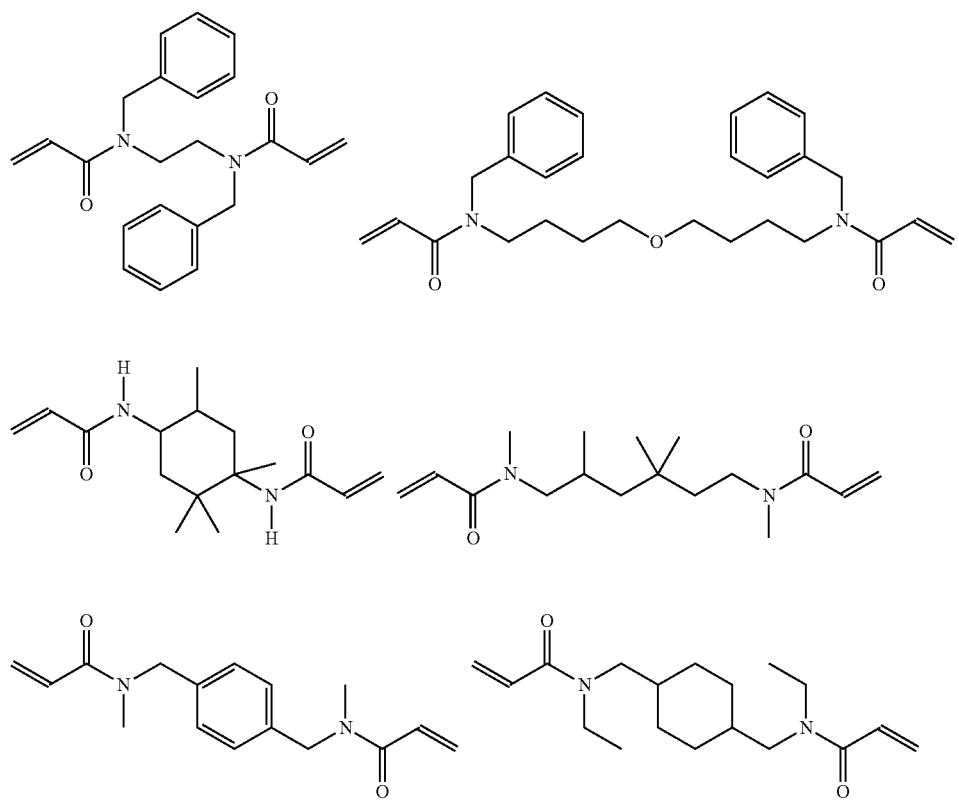

-continued
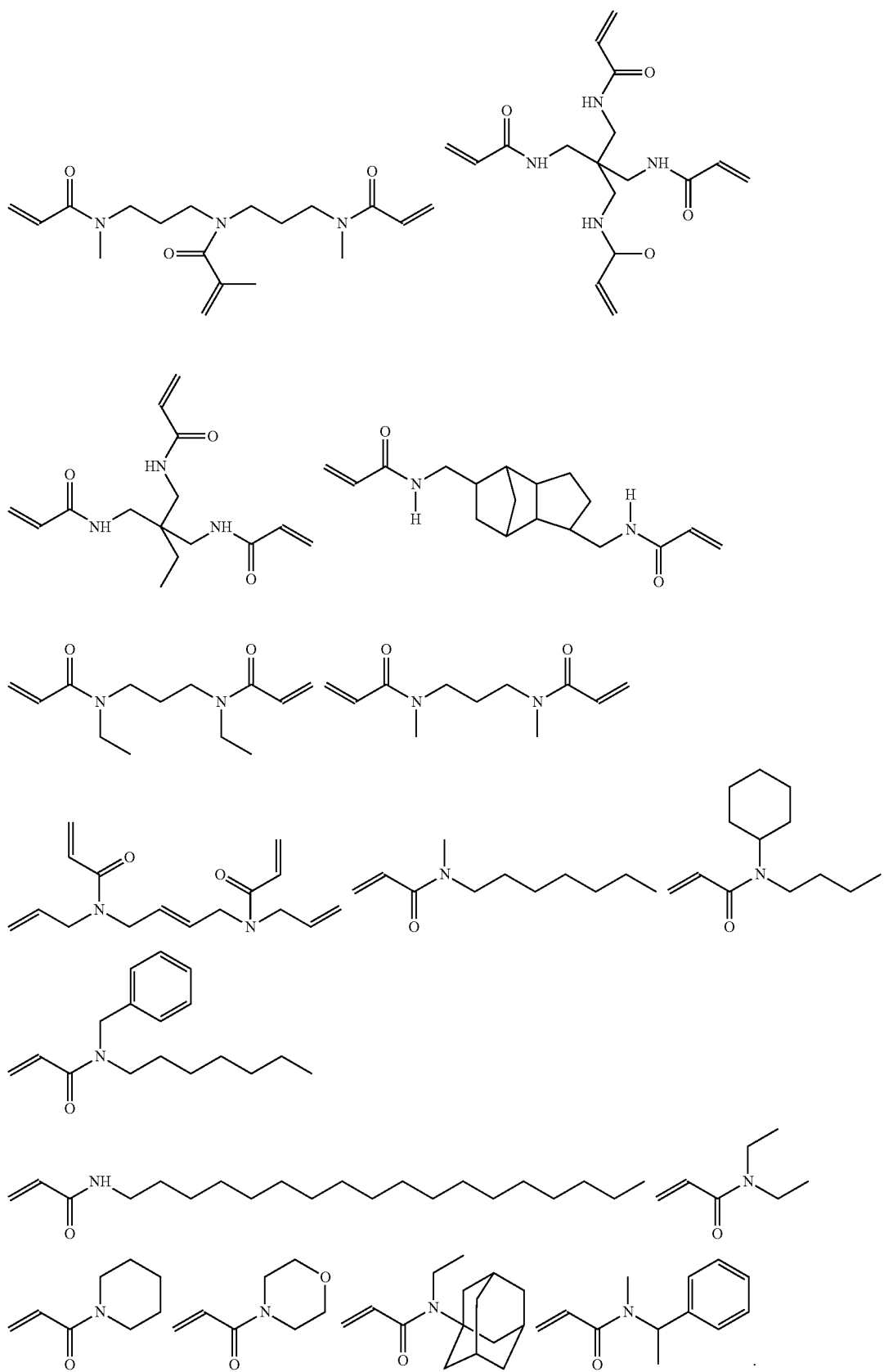

Most preferred are the bis-(meth)acrylamides:
N,N'-diallyl-1,4-bisacrylamido-(2E)-but-2-en (BAABE) having the structural formula

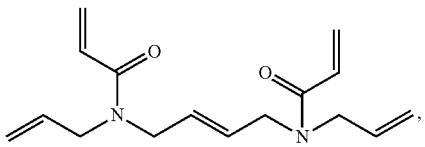 [SMILES: C=CCN(C/C=C/CN(CC=C)C(=O)C=C)C(=O)C=C]

and
N,N'-diethyl-1,3-bisacrylamido-propan (BADEP) having the structural formula

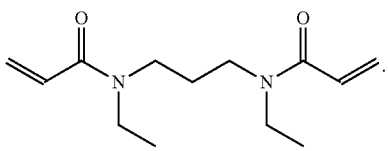 [SMILES: C=CC(=O)N(CC)CCCN(CC)C(=O)C=C]

Compounds having a (meth)acryloyl group or a (meth)acrylamide group also preferably be selected from phosphoric acid ester group containing polymerizable compounds having at least one polymerizable double bond preferably have the following formula (G):

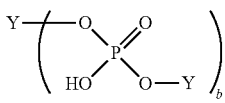

(G)

wherein
the moieties Y independent from each other represent a hydrogen atom or a moiety of the following formulae (Y*), (Y) or (Y*):

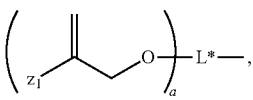

(Y*)

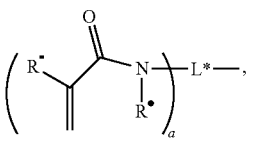

(Y**)

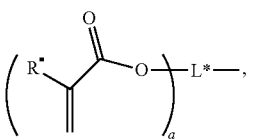

(Y***)

wherein
$Z_1$ is $COOR^\alpha$, $COSR^\beta$, $CON(R^\alpha)_2$, $CONR^\alpha R^\beta$, or $CONHR^\alpha$, wherein $R^\alpha$ and $R^\beta$ independently represent a hydrogen atom, a $C_{1-18}$ alkyl group optionally substituted by a $C_{3-8}$ cycloalkyl group, an optionally substituted $C_{3-8}$ cycloalkyl group, an optionally substituted $C_{4-18}$ aryl or heteroaryl group, an optionally substituted $C_{5-18}$ alkylaryl or alkylheteroaryl group, or an optionally substituted $C_{7-30}$ aralkyl group, whereby two $R^{13}$ residues may form together with the adjacent nitrogen atom to which they are bound a 5- to 7-membered heterocyclic ring which may contain further nitrogen atoms or an oxygen atoms, and whereby the optionally substituted groups may be substituted by 1 to 5 $C_{1-5}$ alkyl group(s);

R* and R** independently represent a hydrogen atom, an optionally substituted $C_{1-18}$ alkyl group, an optionally substituted $C_{3-18}$ cycloalkyl group, an optionally substituted $C_{5-18}$ aryl or heteroaryl group, an optionally substituted $C_{5-18}$ alkylaryl or alkylheteroaryl group, an optionally substituted $C_{7-30}$ aralkyl group, whereby the optionally substituted groups may be substituted by 1 to 5 $C_{1-5}$ alkyl group(s);

L* represents an (a+b)-valent organic residue (whereby b is 1 when Y in formula (D) is within the round brackets) containing 2 to 45 carbon atoms and optionally heteroatoms such as oxygen, nitrogen and sulfur atoms, the carbon atoms including a+b carbon atoms selected from primary and secondary aliphatic carbon atoms, secondary alicyclic carbon atoms, and aromatic carbon atoms, each of the a+b carbon atoms linking a phosphate or a moiety of any one of formula (Y*), (Y) and (Y*); a is an integer of from 1 to 10, preferably 1 to 5; b is an integer of from 1 to 10, preferably 1 to 5; provided that at least one Y is not hydrogen. The preparation of such compounds wherein Y=Y* is known from EP 1 548 021 A1.

Furthermore, compounds having a (meth)acryloyl group or a (meth)acrylamide group may also be selected from phosphonic acid group containing polymerizable acidic compounds of the following formula (H):

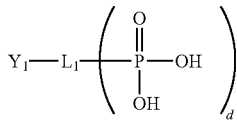

(H)

wherein
the moiety $Y_1$ represents a moiety of the following formulae ($Y_1$) or ($Y_1$*):

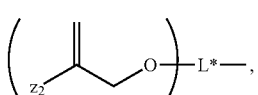

($Y_1$*)

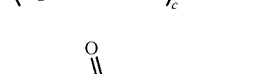

($Y_1$**)

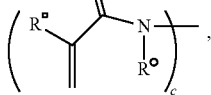

($Y_1$***)

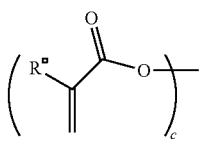

$Z_2$ independently has the same meaning as defined for $Z_1$;
$R^\square$ and $R^\circ$ independently have the same meaning as defined for $R^\blacksquare$ and $R^\bullet$;

$L_1$ represents a (c+d) valent organic residue containing 2 to 45 carbon atoms and optionally heteroatoms such as oxygen, nitrogen and sulfur, the carbon atoms including c+d carbon atoms selected from primary and secondary aliphatic carbon atoms, secondary alicyclic carbon atoms, and aromatic carbon atoms, each of the c+d carbon atoms linking a phosphonate or a moiety of any one of formula $(Y_1^*)$, $(Y_1^{})$ and $(Y_1^{*})$; and c and d independently represent integers of from 1 to 10.

From compound of formula (G'), the following formulae are particularly preferred:

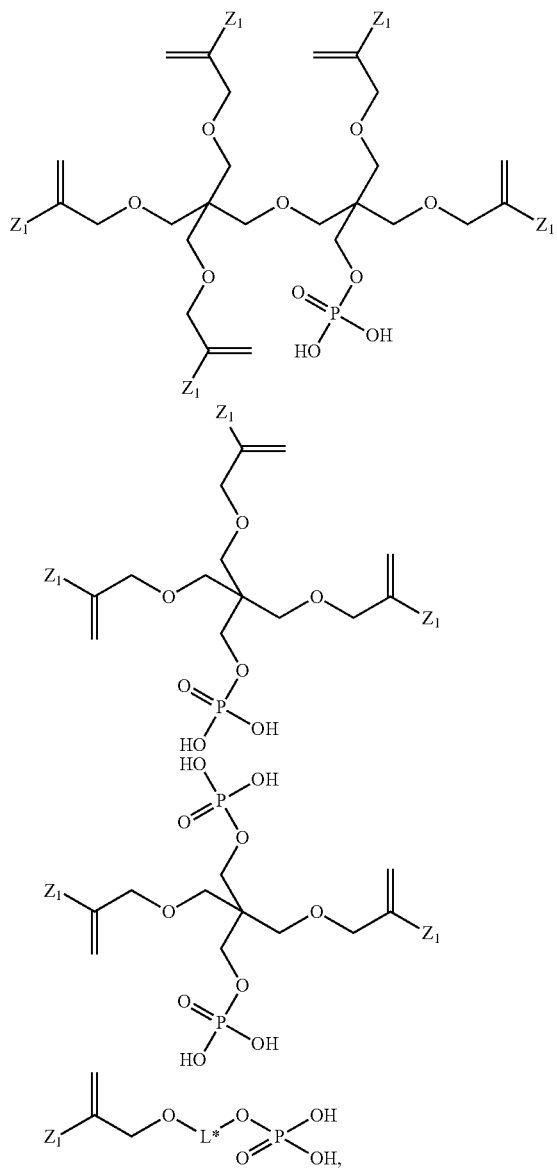

wherein $Z_1$ is defined as above, and L* is an optionally substituted alkylene group. More preferably, $Z_1$ is methyl, and L* is a $C_4$ to $C_{16}$ alkylene group. Even more preferably, L* is a $C_8$ to $C_{12}$ alkylene group.

Furthermore, compounds having one or more radically polymerizable carbon-carbon double bonds may be selected from the hydrolysis stable polyfunctional polymerizable monomers disclosed in EP 2 705 827 and EP 2 727 576.

Particularly preferred compounds having one or more radically polymerizable carbon-carbon double bonds are selected from the compounds of formulae (A), (B), (C), (G), (H), more preferably from the compound of formulae (A), (B), (C), and most preferably from compounds of formula (B).

The optionally further contained compound(s) having one or more cationically polymerizable groups are not particularly limited. However, preferably, their cationically polymerizable groups are selected from epoxide groups, oxetane groups, vinyl ether groups, aziridine groups, and azetidine groups, more preferably from epoxide groups, oxetane groups and vinyl ether groups, and most preferably from epoxide groups and vinyl ether groups.

A compound having one or more cationically polymerizable groups in the form of an epoxide and/or oxetane group may be preferably selected from the compounds of the formulae (J), (K), (L):

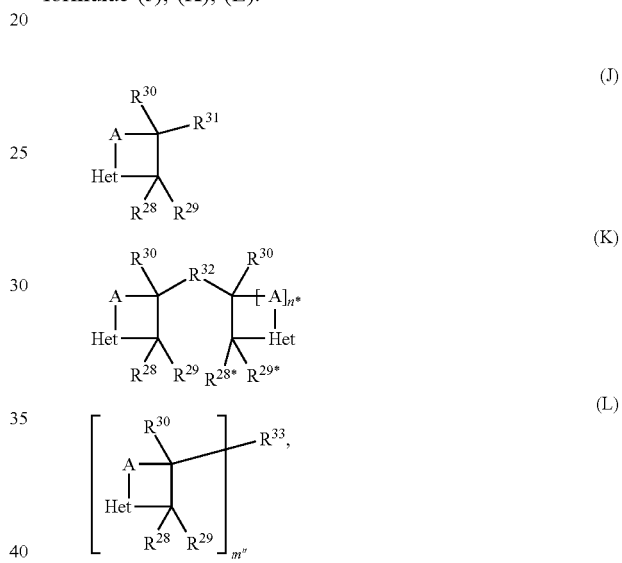

wherein

A is a single bond, a methylene ($-CH_2-$) group or a $-R^{28}CR^{29}-$ in which $R^{28}$ and $R^{29}$ have the same meaning as defined below for $R^{28}$ and $R^{29}$, preferably A is a single bond or a methylene ($-CH_2-$) group, most preferably A is a single bond, Het is an oxygen atom or a nitrogen atom, preferably an oxygen atom, $R^{28}$, $R^{29}$, $R^{30}$, $R^{28*}$, $R^{29*}$, $R^{30*}$, $R^{31}$ independently represent a hydrogen atom, $-COOM$, or an organic moiety selected from the group consisting of a linear $C_{1-18}$ or branched or cyclic $C_{3-18}$ alkyl group which may be substituted by a $C_{3-6}$ cycloalkyl group, a $C_{6-14}$ aryl or $C_{3-14}$ heteroaryl group, $-COOM$, $-PO_3M$, $-O-PO_3M_2$ or $-SO_3M^*$, a $C_3$ to $C_{18}$ cycloalkyl group which may be substituted by a linear $C_{1-16}$ or branched or cyclic $C_{3-16}$ alkyl group, a $C_{6-14}$ aryl or $C_{3-14}$ heteroaryl group, $-COOM$, $-PO_3M$, $-O-PO_3M_2$ or $-SO_3M^*$, or a $C_5$ to $C_{18}$ aryl or $C_3$ to $C_{18}$ heteroaryl group which may be substituted by $-COOM$, $-PO_3M$, $-O-PO_3M_2$ or $-SO_3M^*$, which organic moiety may be substituted with one or more substituent(s) selected from the group consisting of, $R^{32}$ represents a divalent organic residue having from 1 to 45 carbon atoms, whereby said organic residue may contain at least one of 1 to 7 $C_{3-12}$ cycloalkylene group(s), 1 to 7 $C_{6-14}$ arylene groups, 1 to 7 carbonyl groups, 1 to 7 carboxyl groups (—(C=O)—O— or —O—(C=O)—), 1 to 7 amide groups (—(C=O)—NH— or —NH—(C=O)—), 1 to 7 urethane groups (—NH—(C=O)—O— or —O—(C=O)—NH—), 1 to 14 heteroatoms selected from silicium, oxygen, nitrogen and sulphur; preferably $R^{32}$ is a $C_1$ to $C_{18}$ alkylene group which may contain at least one of 1 to 4 carboxyl groups (—(C=O)—O— or —O—(C=O)—)) or at least one moiety —SiR$^\bullet_2$—O—SiR$^\bullet_2$— wherein R$^\bullet$ independently represent a linear $C_{1-4}$ or branched $C_3$ or $C_4$ alkyl group, which divalent organic residue may be substituted with one or more group selected from the group consisting of —OH, —SH, —COOM, —PO$_3$M, —O—PO$_3$M$_2$ or —SO$_3$M*;

and $R^{33}$ represents a saturated di- or multivalent substituted or unsubstituted linear $C_1$ to $C_{18}$ hydrocarbon group, a saturated di- or multivalent substituted or unsubstituted branched or cyclic $C_3$ to $C_{18}$ hydrocarbon group, a di- or multivalent substituted or unsubstituted $C_6$ to $C_{18}$ aryl or heteroaryl group, a di- or multivalent substituted or unsubstituted $C_5$ to $C_{18}$ alkylaryl or alkylheteroaryl group, a di- or multivalent substituted or unsubstituted $C_7$ to $C_{30}$ aralkyl group, or a di- or multivalent substituted or unsubstituted $C_2$ to $C_{45}$ mono-, di-, or polyether residue having from 1 to 14 oxygen or sulphur atoms, and m" is an integer, preferably in the range from 1 to 10, wherein M of any one $R^{28}$, $R^{29}$, $R^{30}$, $R^{28*}$, $R^{29*}$, $R^{30*}$, $R^{31}$ and $R^{32}$, which M are independent from each other, each represent a hydrogen atom or a metal atom, and M* of any one $R^{28}$, $R^{29}$, $R^{30}$, $R^{28*}$, $R^{29*}$, $R^{30*}$, $R^{31}$ and $R^{32}$, which M are independent from each other, each represent a metal atom.

In compound of formulae (J), (K) and (L), $R^{28}$, $R^{30}$ and $R^{28*}$, $R^{30*}$ independently may cooperatively form a ring in which $R^{28}$, $R^{30}$ and $R^{28*}$, $R^{39*}$ are linked by a C—C bond or a functional group selected from the group consisting of an ether group, a thioether group, an amine group and an amide group. Preferably, $R^{28}$, $R^{30}$ and $R^{28*}$, $R^{30*}$ are linked by a C—C bond and form, together with the C—C bond located between $R^{28}$, $R^{30}$ and $R^{28*}$, $R^{30*}$ a 3 to 8 membered ring, preferably a 5 to 7 membered ring, most preferably a $C_6$ ring.

For $R^{32}$, the phrase "divalent organic residue may contain at least one of . . . " has an analogous meaning as defined above for $R_{22}$ of compound of formula (B).

It is preferred that in formula (J), Het is oxygen, $R^{28}$ and $R^{29}$ independently represent a linear $C_{1-8}$ or branched or cyclic $C_{3-8}$ alkyl group which may be substituted with one or more —OH groups. More preferably, in formula (J), Het is oxygen, $R^{28}$ and $R^{29}$ independently represent a linear $C_{1-8}$ alkyl group which may be substituted with one or more —OH groups, and $R^{30}$ and $R^{31}$ represent hydrogen atoms, wherein A is preferably a methylene (—CH$_2$—) group.

It is preferred that in formula (K), A is a single bond, Het is oxygen, $R^{28}$, $R^{30}$ and $R^{28*}$, $R^{30*}$ independently cooperatively form a ring in which $R^{28}$, $R^{30}$ and $R^{28*}$, $R^{39*}$ are linked by a C—C bond, and $R^{32}$ is a $C_1$ to $C_8$ alkylene group which may contain at least one of 1 to 4 carboxyl groups (—(C=O)—O— or —O—(C=O)—)) or at least one moiety —SiR$^\bullet_2$—O—SiR$^\bullet_2$— wherein R$^\bullet$ independently represent a linear $C_{1-4}$ or branched $C_3$ or $C_4$ alkyl group.

Preferably, compounds of formulae (J) and (K) are selected from the group consisting of:

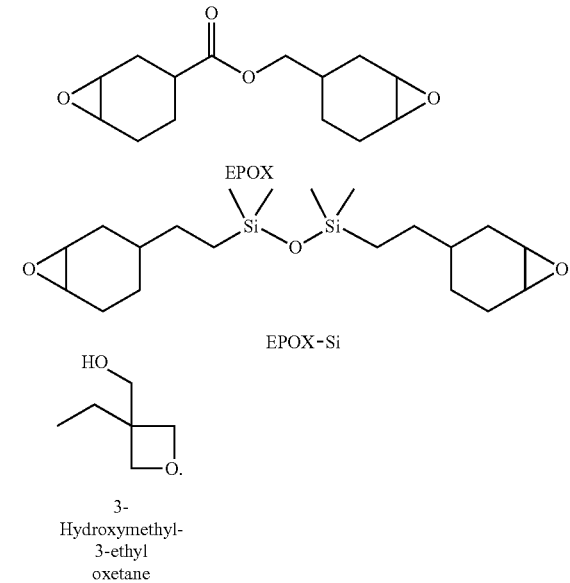

Most preferred are compounds of formula (K) being EPOX and/or EPOX-Si.

A compound having one or more cationically polymerizable groups in the form of a vinyl ether group may be preferably selected from the compounds of the formulae (M), (N), (O):

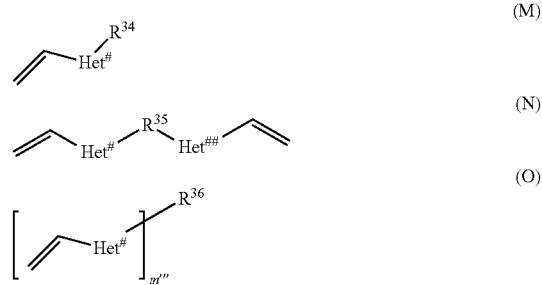

$R^{34}$ has the same meaning as $R^{21}$ defined above for formula (A) or may alternatively represent a monovalent substituted or unsubstituted $C_2$ to $C_{45}$ mono-, di-, or polyether residue having from 1 to 14 oxygen atoms, $R^{35}$ has the same meaning as $R^{22}$ defined above for formula (B), and $R^{36}$ and m'" have the same meaning as $R^{23}$ and m' as defined above for formula (C).

Preferably, in compound of formula (M), Het$^\#$ is an oxygen atom and $R^{34}$ represents a linear $C_{1-14}$ or branched or cyclic $C_{3-14}$ alkyl group, or an ethylenglycol moiety of formula —[—O—CH$_2$—CH$_2$—]$_n$—R$^\gamma$ with n=1 to 9 and R$^\gamma$ being hydrogen or OH.

Preferably, in compound of formula (N), Het$^\#$ and Het$^{\#\#}$ are oxygen atoms and $R^{35}$ represents a $C_1$ to $C_{18}$ alkylene group which may contain at least one of 1 to 4 $C_{3-8}$ cycloalkylene group or 1 to 9 oxygen atoms, wherein the oxygen atoms may be contained such that an ethylenglycol moiety of formula —[—O—CH$_2$—CH$_2$—]$_n$— with n=1 to 9 is formed.

Most preferably, compounds of formulae (M) and (N) are selected from the group consisting of:

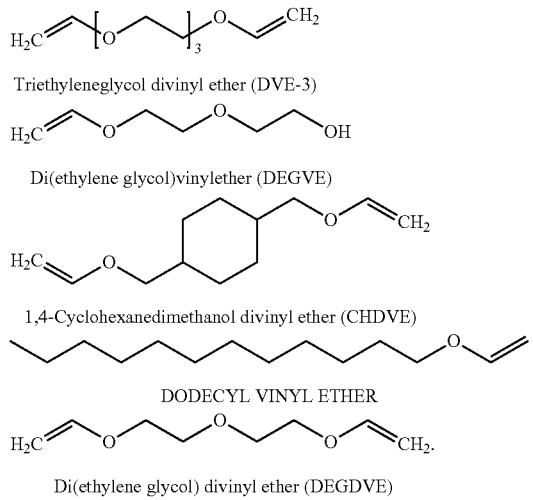

Triethyleneglycol divinyl ether (DVE-3)

Di(ethylene glycol)vinylether (DEGVE)

1,4-Cyclohexanedimethanol divinyl ether (CHDVE)

DODECYL VINYL ETHER

Di(ethylene glycol) divinyl ether (DEGDVE)

Particularly preferred compounds having one or more cationically polymerizable groups are selected from the compounds of formulae (J), (K), (M) and (N), more preferably from the compounds of formulae (K), (M) and (N).

The optionally further contained compound having a combination of at least one radically polymerizable carbon-carbon double bonds and at least one cationically polymerizable group(s) is not particularly limited. However, preferably, in such compound, the radically polymerizable carbon-carbon bonds are selected from (meth)acryloyl group(s) and (meth)acrylamide group(s), and the cationically polymerizable groups are selected from epoxide groups, oxetane groups, vinyl ether groups, aziridine groups, and azetidine groups. More preferably, in such compound, the radically polymerizable carbon-carbon bond(s) is/are (meth)acrylamide group(s), and the cationically polymerizable groups are selected from vinyl ether groups, epoxide groups and oxetane groups. Most preferably, the cationically polymerizable group(s) is/are vinyl ether group(s) and/or epoxide group(s).

A compound having a combination of at least one radically polymerizable carbon-carbon double bonds and at least one cationically polymerizable group(s) may preferably be selected from the compounds of formula (P):

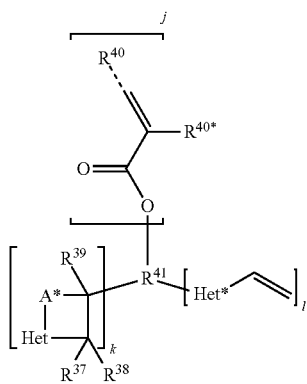

(P)

$R^{37}$, $R^{38}$, $R^{39}$ have the same meaning as $R^{28}$, $R^{29}$, $R^{30}$ defined above for formulae (J), (K) and (L), $R^{40}$, $R^{40*}$ have the same meaning as $R_{20}$ and $R_{20}*$ defined above for formulae (A), (B) and (C), $R^{41}$ has the same meaning as $R_{23}$ defined above for formula (C), j is an integer of 0 to 6, preferably 1 to 3,
k is an integer of 0 to 6, preferably 0 to 3,
j is an integer of 0 to 6, preferably 0 to 3,
with the proviso that j+k+l≥2.

In formula (P), the dotted bond indicates that $R^{40}$ may be in (Z) or (E) configuration relative to CO.

In formula (P), $R^{37}$ and $R^{39}$ may cooperatively form a ring as defined above for $R^{28}$ and $R^{30}$ of formulae (G) and (H).

Most preferably, in compound (P), the radically polymerizable carbon-carbon bond(s) is/are (meth)acrylamide group(s), and the cationically polymerizable groups are vinyl ether groups.

It is preferred that in compound of formula (P), j=1 to 3, k=0 and j=1 to 3, $R^{40}$ is a hydrogen atom, $R^{40*}$ is a linear $C_{1-8}$ or branched or cyclic $C_{3-8}$ alkyl group, $R^{41}$ represents a $C_1$ to $C_{18}$ alkylene group which may contain 1 to 9 oxygen atoms, wherein the oxygen atoms may be contained such that an ethylenglycol moiety of formula —[—O—$CH_2$—$CH_2$—]$_n$— with n=1 to 9 is formed.

A particularly preferred compound of formula (P) is 2-vinyloxyethoxyethyl methacrylate (VEEM) having the following structural formula:

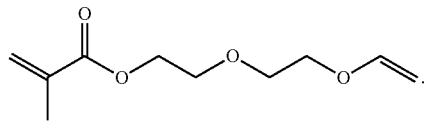

Preferably, the dental composition comprises a homogeneous phase comprising monomer combinations (x) and (y), (x) and (z), (y) and (z), or (x), (y) and (z), or comprising monomer (z), wherein (x) represents one or more compounds having at least one radically polymerizable carbon-carbon double bond;
(y) represents one or more compounds having at least one cationically polymerizable group;
(z) represents one or more compounds having a combination of at least one radically polymerizable carbon-carbon double bond and at least one cationically polymerizable group.

The term "homogeneous phase" means that monomer combinations (x) and (y), (x) and (z), (y) and (z), or (x), (y) and (z), or monomer(s) (z) are present in a single phase without detectable phase boundaries within the single phase.

The term "monomer(s)" as used herein means a compound having a polymerizable group.

The term "interpenetrating polymer network (IPN)" as used herein means that two or more polymers are at least partially interlaced on a molecular scale, but not covalently bonded to each other and cannot be separated unless chemical bonds are broken. A mixture of two or more pre-formed polymers does not represent an IPN. If the two or more polymers of the IPN are formed of compounds having two or more polymerizable groups, then the IPN is according to the official IUPAC definition: "a polymer comprising two or more networks which are at least partially interlaced on a molecular scale, but not covalently bonded to each other and cannot be separated unless chemical bonds are broken". If one or more polymer(s) is/are formed of a compound having two or more polymerizable groups, and one or more polymer(s) is/are formed of a compound having a single polymerizable group, then the IPN is, according to the IUPAC definition, a so-called "semi-interpenetrating polymer network (SIPN): "a polymer comprising on or more networks and one or more linear or branched polymer(s) characterized by the penetration on a molecular scale of at least one of the networks by at least some of the linear of branched macromolecules". The present general definition of IPN includes the IPNs and SIPNs according to IUPAC definition, but also two or more linear or branchend polymers which are at least partially interlaced on a molecular scale, but not covalently bonded to each other, and which cannot be separated unless chemical bonds are broken.

The radically polymerizable carbon-carbon double bonds and cationically polymerizable groups of monomers (x), (y) and (z) are not particularly limited. Preferably, radically polymerizable carbon-carbon double bonds are selected from carbon-carbon double bonds of (meth)acryloyl group(s) and a (meth)acrylamide group(s), preferably (meth)acryloyl group(s). Further, it is preferred that the cationically polymerizable groups are selected from epoxide groups, oxetane groups, vinyl ether groups, aziridine groups, and azetidine groups, preferably from epoxide groups, vinyl ether groups and oxetane groups, most preferably from epoxide groups and vinyl ether groups.

Preferably, the dental composition comprises a homogeneous phase comprising monomer combinations (x) and (y), (x) and (z), (y) and (z), or (x), (y) and (z), most preferably monomer combinations (x) and (y), (x) and (z), or (x), (y) and (z).

For example, monomer(s) (x) may be selected from the acidic polymerizable compound of formula (I) and compounds of formula (A), (B), (C), (D), (E), (F), (G) and (H), monomer(s) (y) may be selected from the acidic polymerizable compound of formula (I) and compounds of formula (J), (K), (L), (M), (N), (O), and monomer(s) (z) may be selected from the acidic polymerizable compound of formula (I) and compound of formula (P).

For the acidic polymerizable compound of formula (I), the polymerizable group $R^1$ and the optional polymerizable group(s) Y and $R^2$ can be suitably selected such that compound of formula (I) complies with one of the definitions for monomers (x), (y) and (z).

Preferably, for monomer(s) (x), at least the acidic polymerizable compound of formula (I) is selected, for monomer(s) (y), any one of compounds of formulae (J) to (O) is selected, and for monomer (z), compound(s) of formula (P) are selected. More preferably, in the aforementioned combination, the acidic polymerizable compound of formula (I) is one wherein $R^1$ represents a (meth)acryloyl group or a (meth)acrylamide group and optionally $R^2$ may represent an alkenyl group such as vinyl or allyl and optionally at least one Y may represent a (meth)acryloyl group or a (meth)acrylamide group, and most preferably, the acidic polymerizable compound of formula (I) is one wherein $R^1$ represents a (meth)acryloyl group and optionally one Y may represent a (meth)acryloyl group.

Alternatively, for monomer(s) (x), any one of compounds of formula (A) to (H) is selected, for monomer(s) (y), any one of compounds of formulae (J) to (O) is selected, and for monomer (z), the acidic polymerizable compound of formula (I) is selected wherein $R^1$ represents a (meth)acryloyl group or a (meth)acrylamide group and optionally $R^2$ may represent an alkenyl group such as vinyl or allyl and at least one Y represents an epoxide group, an oxetane group, a vinyl ether group, an aziridine group or an azetidine group. More preferably, in the aforementioned combination, the acidic polymerizable compound of formula (I) is one wherein $R^1$ represents a (meth)acryloyl group or a (meth)acrylamide group and at least one Y represents an epoxide group, an oxetane group or a vinyl ether group, and most preferably, the acidic polymerizable compound of formula (I) is one wherein $R^1$ represents a (meth)acryloyl group and one Y represents an epoxide group or a vinyl ether group.

Preferably, the homogeneous phase comprises one or more compound(s) (x) and/or (y) having two or more polymerizable carbon-carbon double bonds or cationically polymerizable groups, and/or one or more compound(s) (z) having at least one polymerizable carbon-carbon double bonds and at least one cationically polymerizable groups. This provides for the formation of a crosslinked polymer network. The formation of a crosslinked polymer network is advantageous, since it imparts additional dimensional/mechanical stability to the IPN formed. More preferably, the homogeneous phase (a) comprises compound(s) (x) having two or more radically polymerizable carbon-carbon bonds selected from the group consisting of acidic polymerizable compounds of formulae (I), (B) and (E), and/or compound(s) (y) having having two or more cationically polymerizable groups selected from the group consisting of compounds of formulae (I), (K) and (O), and/or compound(s) (z) having at least one radically polymerizable carbon-carbon double bond and at least one cationically polymerizable group selected from compounds of formulae (I) and/or compounds of formula (P).

For a homogeneous phase comprising compound(s) (x), it is preferred that the homogeneous phase (a) contains components (x), (y) and (z) in a weight ratio (x)/((y)+(z)) of from 0.1 to 10.

Further Optional Components

The dental composition according to the present invention may, besides of the above described optional components, comprise additional optional components.

For example, the dental composition according to the present invention may comprise suitable solvents. These solvents may be selected from water, alcohols such as methanol, ethanol, propanol (n-, i-), butanol (n-, iso-, tert.-), and ketones such as acetone or the like.

The dental composition of the present invention may comprise the solvent in an amount of 5 to 75 percent by weight based on the total weight of the composition.

Besides, the dental composition according to the present invention may comprise suitable particulate fillers. These particulate fillers may be selected from fillers currently used in dental compositions. The filler should be finely divided and preferably has a maximum particle diameter less than about 10 μm and an average particle diameter less than about 1 μm. The filler may have a unimodal or polymodal (e.g., bimodal) particle size distribution.

The filler can be an inorganic material. It can also be a crosslinked organic material that is insoluble in the polymerizable resin, and is optionally filled with inorganic filler. The filler can be radioopaque. Examples of suitable particulate inorganic fillers are naturally-occurring or synthetic materials such as quartz, nitrides such as silicon nitride, glasses derived from, for example Ce, Sb, Sn, Zr, Sr, Ba and Al, colloidal silica, feldspar, borosilicate glass, kaolin, talc, titania, and zinc glass, and submicron silica particles such as pyrogenic silicas. Examples of suitable non-reactive organic filler particles include filled or unfilled pulverized polycarbonates or polyepoxides. Preferably the surface of the filler particles is treated with a coupling agent in order to enhance the bond between the filler and the matrix. The use of suitable coupling agents include gamma-methacryloxypropyltrimethoxysilane, gamma-mercaptopropyltriethoxysilane, gamma-aminopropyltrimethoxysilane, and the like.

The particulate filler may also be a filler obtainable by a process for the preparation of composite filler particles, comprising:

(A) coating a particulate filler having a median particle size (D50) of from 1 to 1200 nm with a coating composition containing a film-forming agent forming a coating layer on the surface of the particulate filler, said coating layer displaying reactive groups on the surface of the coating layer, said reactive groups being selected from addition polymerizable groups and step-growth polymerizable groups, thereby forming a coated particulate filler; subsequently or concurrently (B) agglomerating the coated particulate filler, optionally in the presence of a further crosslinking agent and optionally in the presence of a further particulate filler not displaying reactive groups, for providing a granulation of the coated particulate filler wherein the granulation contains the coated particulate filler particles and the optional further particulate filler particles separated from and connected to each other by at least one coating layer, whereby the at least one coating layer may be crosslinked by crosslinking groups obtained by reacting the reactive groups and optionally a further crosslinking agent;

(C) optionally milling, classifying and/or sieving the granulation of the coated particulate filler; and (D) optionally further crosslinking the granulation of the coated particulate filler; for providing composite filler particles having a median particle size (D50) of from 1 to 70 μm, wherein reactive groups are transformed into crosslinking groups obtained by reacting reactive groups and optionally a further crosslinking agent, and wherein the particulate filler is the main component by volume of the composite filler particles as further described in EP-A 2 604 247.

The dental composition of the present invention may preferably comprise 0.1 to 85 percent by weight based on the total weight of the composition of particulate filler.

The dental composition of the present invention may further contain preservatives, pigments, free radical scavengers, reactive and nonreactive diluents, coupling agents to enhance reactivity of fillers, rheology modifiers, and surfactants.

Suitable preservatives may be selected from reducing agents such as vitamin C, inorganic sulfides and polysulfides and the like.

The acidic polymerizable compound of formula (I) as defined in claim 1 may be used for the preparation of a dental composition, preferably of a dental composition according to the invention as described above.

The invention will now be further illustrated by the following Examples.

EXAMPLES

Synthesis of a N-acryloyl phosphoglycoside According to Formula (I) (Wherein Z=Oxygen Atom, $R_1$=Acryloyl and $R_2$=H)

General Procedure

A mono- or disaccharide and an catalytic amount of a Lewis acid (such as $BF_3OEt_2$ or TMSOTf, in general in amounts of 5 to 10 mol %) was added to an excess of an azidoalcohol (8-16 equiv.) and stirred at 80° C. for 12 to 24 hours. The resulting azidoglycoside was purified by column chromatography, and then dissolved in ethanol. A catalytic amount of palladium on charcoal (10 wt. % Pd on C, 5% by weight) was added, and the resulting reaction mixture was stirred under hydrogen for 12-48 hours. After filtration, equimolar amounts of an organic base (such as triethylamine or diisopropylethylamine) was added, and the mixture was cooled to 5° C. Then, an equimolar amount of acryloylchloride was added dropwise, and the mixture was stirred for 1 to 2 hours.

Aqueous workup yields the acryloylglycoside, which was phosphorylated by dissolving in THF and addition of one equivalent of an organic base (such as triethylamine or diisopropylamine) and one equivalent of phorphoroxychloride ($POCl_3$) per hydroxyl group. This mixture was stirred overnight, and then washed with brine, dried and evaporated to yield the desired N-acryloyl phosphoglycoside according to formula (I).

Synthesis of a N-allyl-acryloyl phosphoglycoside According to Formula (I) (Wherein Z=Oxygen Atom, $R_1$=Acryloyl and $R_2$=Allyl)

General Procedure

A bromoalcohol (such as hexanolbromide) was stirred in 5 to 10 equivalent of allylamine in presence of 1.2 equiv. of a base such as potassium carbonate for 16 to 24 hours. After filtration the excess of potassium carbonate, allylamine was removed.

A mono- or disaccharide and an catalytic amount of a Lewis acid (such as $BF_3OEt_2$ or TMSOTf, in general in amounts of 5 to 10 mol %), was added to an excess of the corresponding allylaminoalcohol (8 to 16 equiv.), and stirred at 80° C. for 12 to 24 hours. The resulting allylaminoglycoside was purified by column chromatography, dissolved in ethanol, and an equimolar amount of an organic base (such as triethylamine or diisopropylethylamine) was added, and the resulting mixture was cooled to 5° C. Then, an equimolar amount of acryloylchloride was added dropwise, and the mixture was stirred for 1 to 2 hours.

Aqueous workup yields the allylacryloylglycoside, which was phosphorylated by dissolving in THF and addition of one equivalent of an organic base (such as triethylamine or diisopropylamine) and one equivalent of phorphoroxychloride ($POCl_3$) per hydroxyl group. This mixture was stirred overnight, and then washed with brine, dried and evaporated to yield the desired N-allyl-acryloyl phosphoglycoside according to formula (I).

Synthesis of aminoglycosidesugaracrylates

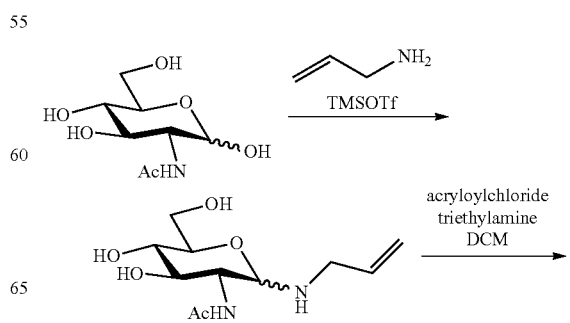

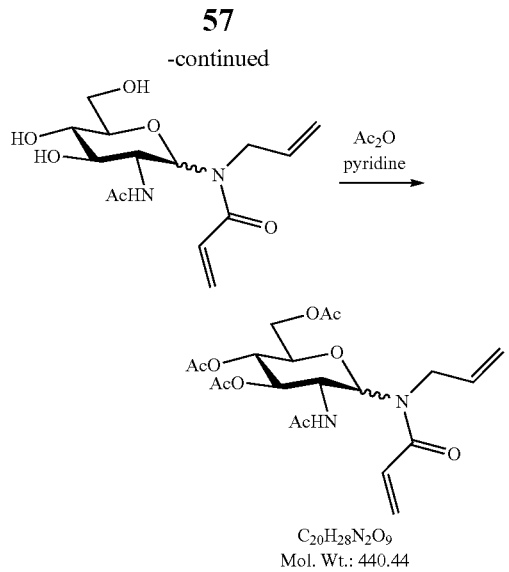

N-Acetylglucosamin (GlcNAc) and a catalytic amount of a Lewis acid (LA, such as BF3OEt2 or TMSOTf, in general in amounts of 5-10 mol %) is added to an excess of allylamine (8-16 equiv.) and stirred at 80° C. for 12-24 hours. The resulting allylaminoglycoside is isolated by evaporation of excess allylamine and used without further purification. Therefore the glycoside is dissolved in DMF/triethylamine (2:1 mixture) and 1 equiv. acryloylchloride is added dropwise at −20° C. The mixture is stirred for 14 hours at −20° C. Then the volatile components are removed, the residue is dissolved in pyridine (15 equiv.) and acetic anhydride (15 equiv.) is added at room temperature. After 5 hours of stirring the excess pyridine and acetic anhydride is evaporated and the crude product is dissolved in DCM, washed twice with 2N HCl, sat. sodiumbicarbonate solution and brine. After drying over sodium sulphate DCM is removed and the residue is purified by column chromatography afterwards the product was isolated in 30% overall yield.

The invention claimed is:

1. A dental composition comprising
   (i) an acidic polymerizable compound of the following formula (Ia), (Ib) or (Ic):

wherein
X which are a same or different, are bonded directly or through a methylene group to the cyclic moiety, independently represent an acidic group selected from a sulfate group, a phosphate group, a sulfonate group, a phosphonate group and a carboxylic acid group;

Y represents, if present, a hydrogen atom, a methyl group, a hydroxyl group, an amino group, a polymerizable group, a thiol group or an amide group, each group Y is bonded directly or through a methylene group to the cyclic moiety;

Y' represents an OH or amide group —NH—(C=O)—$R^3$, and

Z represents a single bond, a carbamate group, a thiocarbamate group, a dithiocarbamate group, a urea group, a thiourea group, an amide group, an oxygen atom, a sulfur atom, or a group NR', wherein R' represents a hydrogen atom, a straight-chain $C_{1-6}$ alkyl group, or a branched or cyclic $C_{3-6}$ alkyl group which may be substituted with a phosphonate group, wherein group Z is bonded directly or through a methylene group to the cyclic moiety, L represents a divalent linker group;

$R^2$ represents a hydrogen atom, a straight-chain $C_{1-20}$ hydrocarbon group, a branched or cyclic $C_{3-20}$ hydrocarbon group, or a polymerizable group;

$R^3$ and $R^4$ independently represent a hydrogen atom, a straight-chain $C_{1-6}$ alkyl group, or a branched or cyclic $C_{3-6}$ alkyl group; and (ii) an initiator system.

2. The dental composition according to claim 1, wherein the acidic polymerizable compound of Formula Ia, Ib or Ic is a glycoside.

3. The dental composition according to claim 1, wherein X is a phosphate group bonded directly or through a methylene group to the cyclic moiety.

4. The dental composition according to claim 1, wherein Y is an amide group bonded directly or through a methylene group to the cyclic moiety.

5. The dental composition according to claim 1, wherein Z is an oxygen atom.

6. The dental composition according to claim 1, wherein L is a divalent $C_{1-20}$ hydrocarbon containing one or more heteroatoms selected from the group of an oxygen atom, a sulfur atom, and a nitrogen atom.

7. The dental composition according to claim 1, wherein $R^2$ represents a hydrogen atom or an allyl group.

8. The dental composition according to claim 1, wherein the acidic polymerizable compound of Formula Ia, Ib or Ic is obtained by a process comprising the steps of:
   (a) reacting a mono- or disaccharide with a halogenoalcohol in the presence of a catalytic amount of a Lewis or Bronsted acid for obtaining an haloglycoside,
   (b) substituting of the halogen of the halogenoglycoside with sodium azide for obtaining an azidoglycoside,
   (c) hydrogenating the azidoglycoside with hydrogen in the presence of a hydrogenation catalyst for obtaining an aminoglycoside, (d) reacting the aminoglycoside with (meth)acryloyl halide for obtaining the corresponding (meth)acylamide, and
(e) phosphorylation of the (meth)acrylamide for obtaining an acidic polymerizable compound of formula Ia, Ib or Ic;

or is obtained by a process comprising the steps of:
(I-1) reacting a mono- or disaccharide with an azidoalcohol in the presence of a catalytic amount of a Lewis or Brønsted acid for obtaining an azidoglycoside, followed by hydrogenating the obtained azidoglycoside with hydrogen in the presence of a hydrogenation catalyst for obtaining an aminoglycoside, or (I-2) reacting a mono- or disaccharide with a halogenoalcohol in the presence of a catalytic amount of a Lewis or Brønsted acid for obtaining a halogenoglyco side, and substituting the halogen of the halogenoglycoside with an alkylamine or alkenylamine for obtaining an alkyl- or alkenyl-aminoglycoside or alkenylaminoglycoside;
(I-3) reacting a mono- or disaccharide with an N-alkyl- or N-alkenylalcohol in the presence of a catalytic amount of a Lewis or Brønsted acid for obtaining an alkyl- or alkenylaminoglycoside (II) reacting the aminoglycoside obtained in step (i-1) or the alkyl- or alkenyl-aminoglycoside obtained in step (I-2) or (I-3) with (meth)acryloyl halide for obtaining the corresponding (meth)acrylamide and (III) phosphorylation of the (meth)acrylamide for obtaining an acidic polymerizable compound of formula Ia, Ib or Ic.

9. The dental composition according to claim 1, wherein at least one of the following features is present:
a) the acidic polymerizable compound of the following formula (Ia), (Ib) or (Ic) is a crosslinker,
b) L is an alkylene(polyoxyalkylene) group or a $C_{2-6}$ alkenylene group,
c) the initiator system is a photoinitiator system, a redox initiator system or a dual cure initiator system, and
d) the dental composition is a dental adhesive composition, a bonding agent, a pit and fissure sealant, a dental desensitizing composition, a pulp capping composition, a dental composite, a flowable dental composite, a dental glass ionomer cement, a dental cement, resin modified glass ionomers, or a dental root canal sealer composition.

10. The dental composition according to claim 8, wherein the process for preparing the acidic polymerizable compound of formula (Ia), (Ib) or is carried out as a one-pot process.

11. The dental composition according to claim 2, wherein the glycoside is a glucoside, a fructoside, a glucuronide, a mannoside, a galactoside, a riboside, an alloside, an altroside, a guloside, an idoside, a taloside, a rhamnoside, a xyloside, a lyxoside, a arabinoside, a ribuloside, a xyluloside, a psicoside, a sorboside, a tagatoside, an erythroside, a threoside, a lactoside, a maltoside, a chitobioside, or a deoxy sugar derivative thereof.

* * * * *